US008287458B2

(12) United States Patent
Vanney et al.

(10) Patent No.: US 8,287,458 B2
(45) Date of Patent: Oct. 16, 2012

(54) CORONARY VENOUS SYSTEM PRESSURE SENSING

(75) Inventors: Guy Vanney, Blaine, MN (US); Scott Salys, Plano, TX (US); Thao Ngo, Shakopee, MN (US); Elizabeth Nee, Chicago, IL (US); Annapurna Karicherla, Valencia, CA (US); Ravisankar Gurusamy, Eagan, MN (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1163 days.

(21) Appl. No.: 12/110,173

(22) Filed: Apr. 25, 2008

(65) Prior Publication Data
US 2009/0270741 A1    Oct. 29, 2009

(51) Int. Cl.
*A61B 5/02* (2006.01)
*A61N 1/00* (2006.01)

(52) U.S. Cl. ........ 600/486; 600/481; 600/485; 600/488; 600/492; 600/509; 607/23

(58) Field of Classification Search ............... 600/481, 600/485, 486, 488, 508, 509, 492; 607/9, 607/17, 23
See application file for complete search history.

(56) References Cited

U.S. PATENT DOCUMENTS

| 5,129,394 | A * | 7/1992 | Mehra ............... 607/23 |
| 6,529,779 | B1 | 3/2003 | Sutton |
| 6,666,826 | B2 * | 12/2003 | Salo et al. .......... 600/485 |
| 2003/0125774 | A1 | 7/2003 | Salo |
| 2007/0151348 | A1 | 7/2007 | Zdeblick et al. |

FOREIGN PATENT DOCUMENTS

| WO | 03057315 A1 | 7/2003 |
| WO | 2006086435 A2 | 8/2006 |

* cited by examiner

*Primary Examiner* — Gail R Gabel

(57) ABSTRACT

Disclose herein is a method of measuring pressures in a coronary sinus. In one embodiment, the method includes: introducing a distal portion of a lead or tool into the coronary sinus, wherein the distal portion includes first and second pressure sensors and at least one selectably expandable member; expanding the at least one expandable member such that the first and second sensors are isolated from each other within the coronary sinus; and taking pressure measurements with the first and second sensors when isolated from each other.

20 Claims, 21 Drawing Sheets

CORONARY VENOUS SYSTEM PRESSURE SENSING

FIELD OF THE INVENTION

The present invention relates to cardiac resynchronization therapy ("CRT"). More specifically, the present invention relates to devices and methods for optimizing CRT and detecting atrial fibrillation and ventricular fibrillation.

BACKGROUND OF THE INVENTION

Currently CRT has an estimated 25-35% non-responder rate. This may be due to poor patient selection, improper placement of the left ventricular pacing lead, a poor pacing vector, or poor atrio-ventricular, inter-ventricular or intra-ventricular electrical stimulation.

Some CRT optimization options currently available to physicians are echocardiography, electrical optimization based on electrical impulse delay, or the placement of pressure sensors in the chambers of the heart. However, these CRT optimization options leave room for improvement. Specifically, there is a need in the art for a device (e.g., a lead or delivery tool) and method that allow a physician to quickly and easily optimize CRT based on left ventricle mechanical or hemodynamic performance.

SUMMARY

Disclosed herein is a method of measuring pressures in a coronary sinus. In one embodiment, the method includes: introducing a distal portion of a lead or tool into the coronary sinus, wherein the distal portion includes a pressure sensing capability and at least one occlusion device; positioning the pressure sensing capability near a first junction of the coronary sinus with a first vein intersecting the coronary sinus; and expanding the at least one occlusion device so the sensor capability primarily reads the pressure of the first vein intersecting the coronary sinus.

Disclose herein is a method of measuring pressures in a coronary sinus. In one embodiment, the method includes: introducing a distal portion of a lead or tool into the coronary sinus, wherein the distal portion includes first and second pressure sensing capabilities and at least one occlusion device; occluding with the at least one occlusion member so the first and second pressure sensing capabilities are isolated from each other within the coronary sinus; and taking pressure measurements with the first and second pressure sensing capabilities when isolated from each other.

Disclosed herein is an implantable medical lead or delivery tool. In one embodiment, the lead or tool includes a tubular body with a distal portion including first and second sensors and first selectably expandable member separating the first and second sensors. The first and second sensors are at least one of pressure sensors, fluid velocity sensors and force sensors.

Disclosed herein is a tool associated with the implantation of an implantable medical lead. In one embodiment, the tool includes: a tubular body with a distal portion; and a pressure sensing capability associated with the distal portion.

Disclosed herein is a method of determining an optimized location for placement of an electrode implanted for cardiac resynchronization therapy. In one embodiment, the method includes: read a baseline rate of change of pressure (dP/dt) in the coronary sinus; read a paced dP/dt in the coronary sinus; and compare paced dP/dt and baseline dP/dt.

Disclosed herein is a method of determining a condition associated with the left ventricle. In one embodiment, the method comprises: read a pressure signal from the coronary sinus; select a number of stable beats from the pressure signal; and determine $dP/dt_{max}$ for the selected beats.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
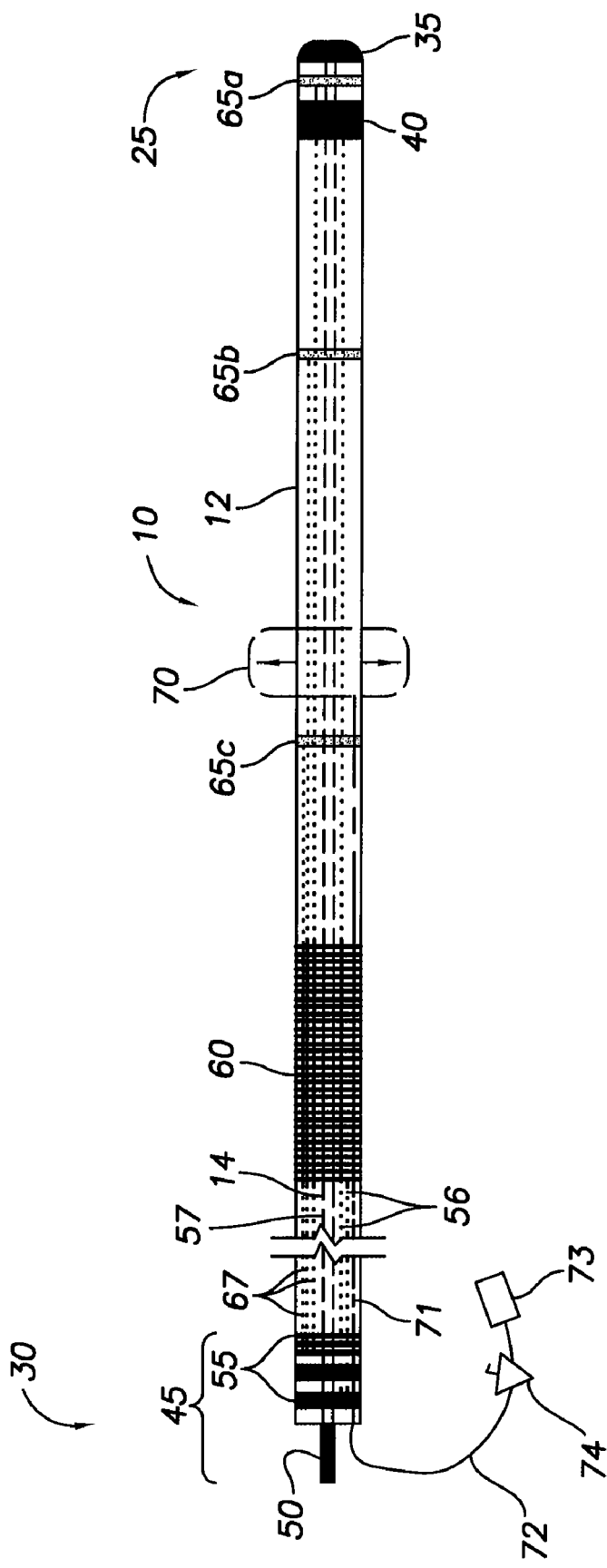
FIG. 1 is a side view of an implantable left ventricle lead.

Disclosed herein are devices and methods that allow a physician to quickly and easily optimize cardiac resynchronization therapy ("CRT") based on left ventricle mechanical or hemodynamic performance, segregate the patient population into CRT-responders and CRT-nonresponders, detect atrial fibrillation ("Afib"), detect ventricular fibrillation ("Vfib"), optimize multi-site left ventricle pacing, optimize right ventricle lead placement and monitor or determine disease progression.

The devices may be in the form of an implantable medical lead 10 or a delivery tool 15 for delivering leads or other medical devices. The devices 10, 15 may incorporate pressure or flow velocity sensors 65 to enable the measurement of venous pressure or blood flow in the coronary sinus ("CS") (i.e., the CS and its related coronary venous anatomy (e.g., great cardiac vein, posterior cardiac vein, left cardiac vein, middle cardiac vein, small cardiac vein, etc.)). Alternatively, the devices 10, 15 may incorporate force sensors 65 to measure the force applied by the myocardium on the device 10, 15. The pressure, flow or force readings may allow the measure of left ventricular function without the introduction of sensors into the left ventricle ("LV") or echocardiographic studies. Thus, the devices 10, 15 can be used to make an acute or chronic assessment of LV function and, as a result, CRT. In acute applications, the pressure data could be used to determine if a patient would respond to CRT. If implanted chronically, the devices could also be used to detect AFib, VFib and monitor cardiac disease progression.

For a discussion regarding a first embodiment of a device for optimizing CRT, reference is made to FIG. 1, which is a side view of an implantable LV lead 10. As shown in FIG. 1, the lead 10 includes a tubular body 12 with a distal end 25 and a proximal end 30. The tubular body 12 may have a central lumen 14 extending the length of the tubular body 12 through which a guidewire or stylet may be extending when deploying the lead 10.

Depending on the embodiment and as is common in the art, a length of the lead body 12 extending proximal of the distal end 25 may be configured for passive fixation in the LV, for example, via a series of humps or bends (not shown) in the lead body 12. The humps or bends bias against the walls of the coronary sinus and associated vascular structures to passively hold the lead distal end 25 in place at the implantation site.

The distal end 25 may include a tip electrode 35 and one or more ring electrodes 40. The tip electrode 35 and/or ring electrodes 40 may be used for sensing and/or pacing.

The proximal end 30 may include a lead connector end 45 for mechanically and electrically coupling the proximal end 30 to a pulse generator, such as a pacemaker, defibrillator or implantable cardioverter defibrillator ("ICD"). The lead connector end 45 may include a contact pin 50 and one or more contact rings 55. The pin 50 and rings 55 make electrical contact with corresponding structures within the pulse generator when the lead connector end 45 is received in the pulse generator. As is common in the art, conductors 56, 57 extend through the lead body to electrically couple the various electrodes 35, 40 to their respective pin 50 or ring 55. One conductor configuration may include a cable conductor 56 extending between a contact ring 55 and a ring electrode 40 and a helical coil conductor 57 lining the lumen 14 and extending between the contact pin 50 and the tip electrode 35.

Proximal of the distal end 25, the lead 10 may include a defibrillation coil 60. Conductors will also extend through the lead body to electrically couple the coil 60 to its respective ring 55. One conductor configuration may include a cable conductor 56 extending between a contact ring 55 and the coil 60.

As indicated in FIG. 1, in one embodiment, the lead 10 will include one, two, three or more sensors 65 along a distal portion of the lead 10. For example, in one embodiment, the lead 10 will include a distal sensor 65a near the distal end 25, an intermediate sensor 65b proximal of the distal sensor 65a, and a proximal sensor 65c proximal of the intermediate sensor 65b. Depending on the embodiment, the sensors 65 may be pressure sensors, force sensors, flow velocity sensors, or a combination of one or more of these sensors. The sensors 65 may be piezo, strain gage, or the like. In a manner similar to the electrodes 35, 40, conductors 67 extend through the lead body 12 to electrically couple the sensors 65 to respective rings 55 at the lead connector end 45. Readings obtained via the sensors 65 can then be used to optimize CRT as discussed later in this Detailed Description.

In one embodiment, the lead 10 may also include one or more expandable balloons 70 on the distal portion of the lead 10. The balloon 70 may be expanded to occlude the body lumen in which the lead is located at the time of balloon expansion. An interior lumen 71 may extend through the lead body from the lead proximal end 30 to the balloon 70. An exterior lumen 72 may be removably coupled to the proximal end of the internal lumen 71. The exterior lumen 72 may include a luer lock 73 and stop valve 74. The luer lock 73 may be used to couple the proximal end of the exterior lumen 72 to an inflation source, which can be used to selectively expand the balloon 70.

In some embodiments, any one or more of the balloons 70 discussed herein may be another type of occlusion device 70. For example, the occlusion device 70 may be of an active type similar to the balloon wherein the physician has to choose to activate the occlusion device. Besides a balloon 70, such an active type occlusion device 70 may include a membrane or mesh expandable via actuation of an actuation device such as a pull/push member, an extendable/retractable outer sheath, a twisting configuration, etc.

In other embodiments, the occlusion device 70 may be of a passive type wherein the physician need not act to bring about the expansion of the device 70. For example, the device may be a one-way valve that is set up to allow blood in the CS to return to the RA. However, the valve would block the RA pressure pulse in the CS by preventing blood in the RA from entering the CS.

While the term balloon 70 is used throughout this Detailed Description, it should be understood that any of the aforementioned occlusion devices 70 may readily be substituted for any one or more of the balloons 70 discussed in the various embodiments disclosed herein. Accordingly, this Detailed Discussion should not be limited only to embodiments employing balloons, but should be considered to encompass embodiments employing all types of occlusion devices 70.

In one embodiment, the balloon 70 is located between two of the sensors 65. For example, the balloon 70 may be located between the intermediate sensor 65b and the proximal sensor 65c. In one such embodiment, the balloon 70 is just distal of the proximal sensor 65c. The advantages of such a configuration will be explained later in this Detailed Description.

Figure 14:
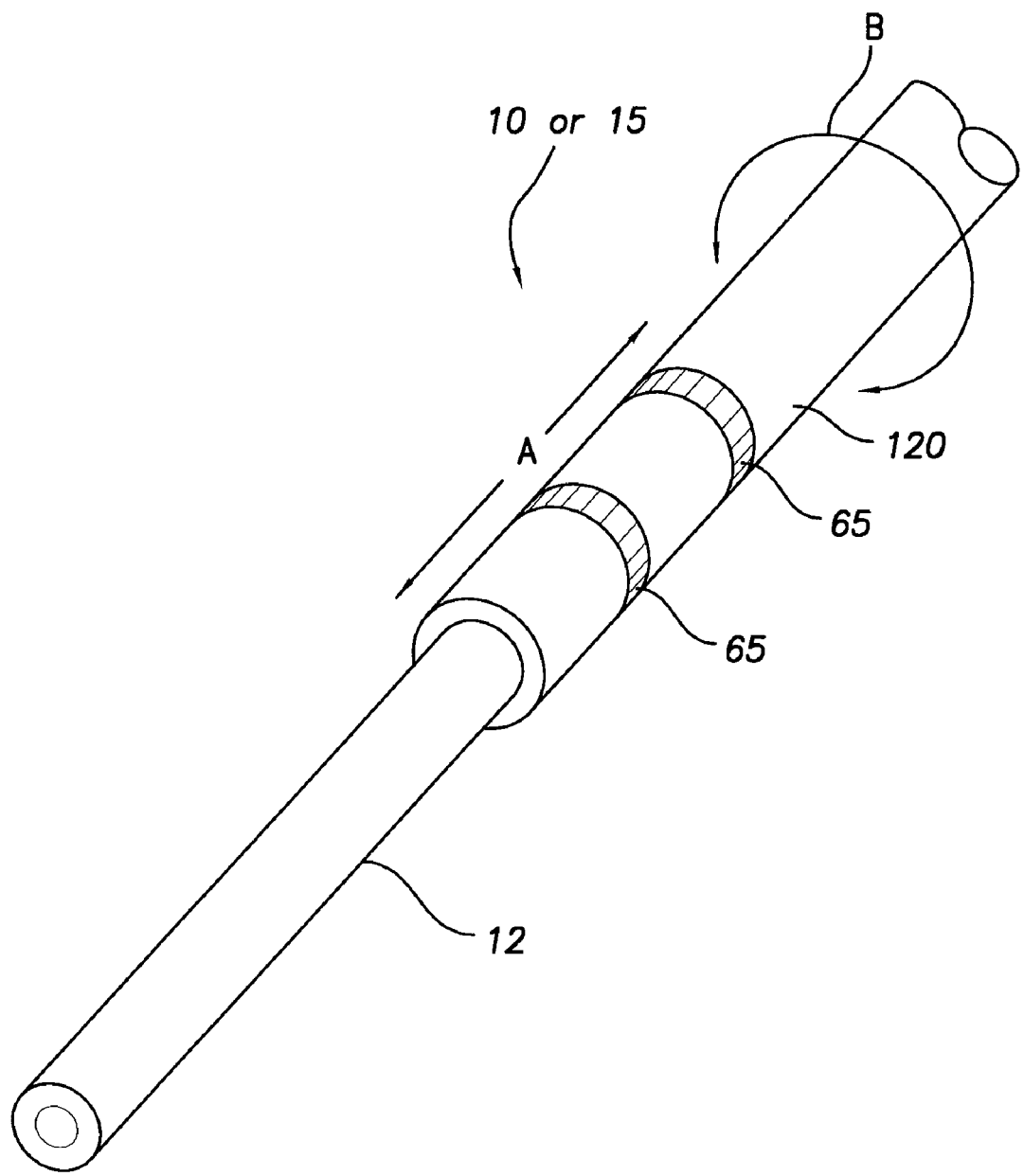
FIG. 14 is an isometric view of a distal portion of a lead or tool having a slidable outer sheath with sensors thereon.

In one embodiment, as can be understood from FIG. 14, the pressure sensors 65 may be mounted on an outer sleeve 120 extending about an outer surface of the body 12 of the lead 10 or introducer 15. The outer sleeve 120 is longitudinally and/or radially displaceable relative to the rest of the body 12 as respectively indicated by arrows A and B. Thus, the sensors 65 may be longitudinally and/or radially repositioned anywhere along the body 12 body. Such a configuration may allow the pressure sensors 65 to be placed in a consistent or desirable location, regardless of where the lead 10 or tool 15 itself is placed.

Figure 2:
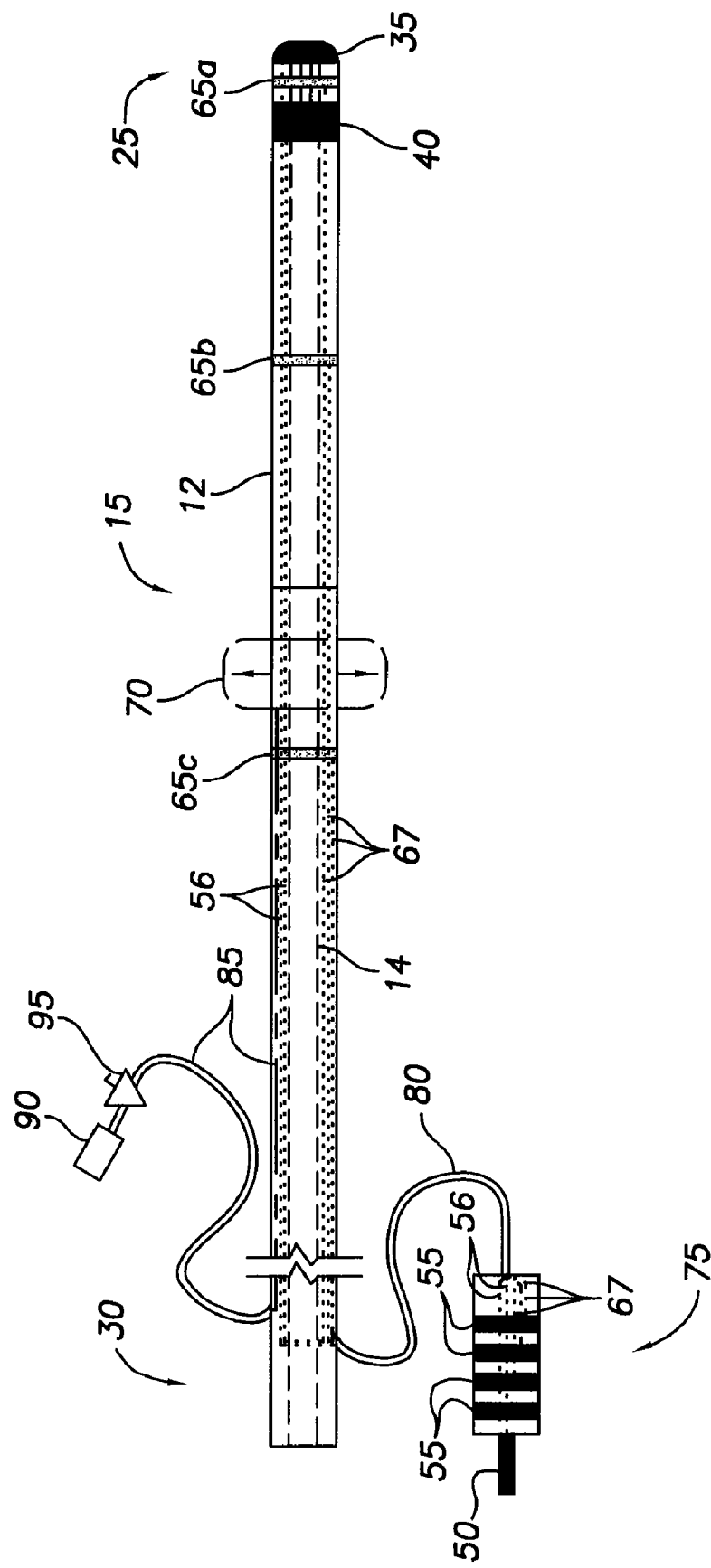
FIG. 2 is a side view of delivery tool, such as a catheter or sheath.

For a discussion regarding a second embodiment of a device for optimizing CRT, reference is made to FIG. 2, which is a side view of delivery tool 15, such as a catheter or sheath, for delivering implantable medical leads or other medical devices. The delivery tool 15 may be a standard introducer sheath or a sub-selector introducer sheath. As shown in FIG. 2, the tool 15 includes a tubular body 12 with a distal end 25 and a proximal end 30. The tubular body 12 has a central lumen 14 extending the length of the tubular body 12 through which a LV lead or other medical device may be passed when deploying the LV lead.

The distal end 25 may include one or more electrodes in the form of a tip electrode 35 and/or one or more ring electrodes 40. The electrodes may be used for sensing electrical signals to determine the proper implantation site for a LV lead being deployed via the delivery tool 15.

A connector 75 may extend from the tool proximal end 30 via a conductor cable 80. The connector 75 may include a contact pin 50 and one or more contact rings 55. As is common in the art, conductors 56 extend through the cable 80 and lead body 12 to electrically couple the various electrodes 35, 40 to their respective pin 50 or ring 55. The connector 75 is mechanically and electrically coupled to diagnostic equipment such that the pin 50 and rings 55 make electrical contact with corresponding structures within the diagnostic equipment. The diagnostic equipment can then be used to interpret readings taken by the sensing electrodes 35, 40.

As indicated in FIG. 2, in one embodiment, the delivery tool 15 will include one, two, three or more sensors 65 along a distal portion of the tool 15. For example, in one embodiment, the delivery tool 15 will include a distal sensor 65a near the distal end 25, an intermediate sensor 65b proximal of the distal sensor 65a, and a proximal sensor 65c proximal of the intermediate sensor 65b. Depending on the embodiment, the sensors 65 may be pressure sensors, force sensors, flow velocity sensors, or a combination of one or more of these sensors. The sensors 65 may be piezo, strain gage, or the like. In a manner similar to the sensing electrodes 35, 40, conductors 67 extend through the tool body 12 and cable 80 to electrically couple the sensors 65 to respective rings 55 at the connector 75. Readings obtained via the sensors 65 can then be used to optimize CRT as discussed later in this Detailed Description.

In one embodiment, the delivery tool 15 will also include one or more expandable balloons 70 on the distal portion of the tool 15. The balloon 70 may be expanded to occlude the body lumen in which the tool is located at the time of balloon expansion. A lumen 85 may extend through the tool body 12 from a luer lock 90 and valve 95 at the tool proximal end 30 to a balloon 70 to place the balloon in fluid communication with an inflation source used to selectively expand the balloon 70.

In one embodiment, the balloon 70 is located between two of the sensors 65. For example, the balloon 70 may be located between the intermediate sensor 65b and the proximal sensor 65c. In one such embodiment, the balloon 70 is just distal of the proximal sensor 65c. The advantages of such a configuration will be explained later in this Detailed Description.

Figure 12:
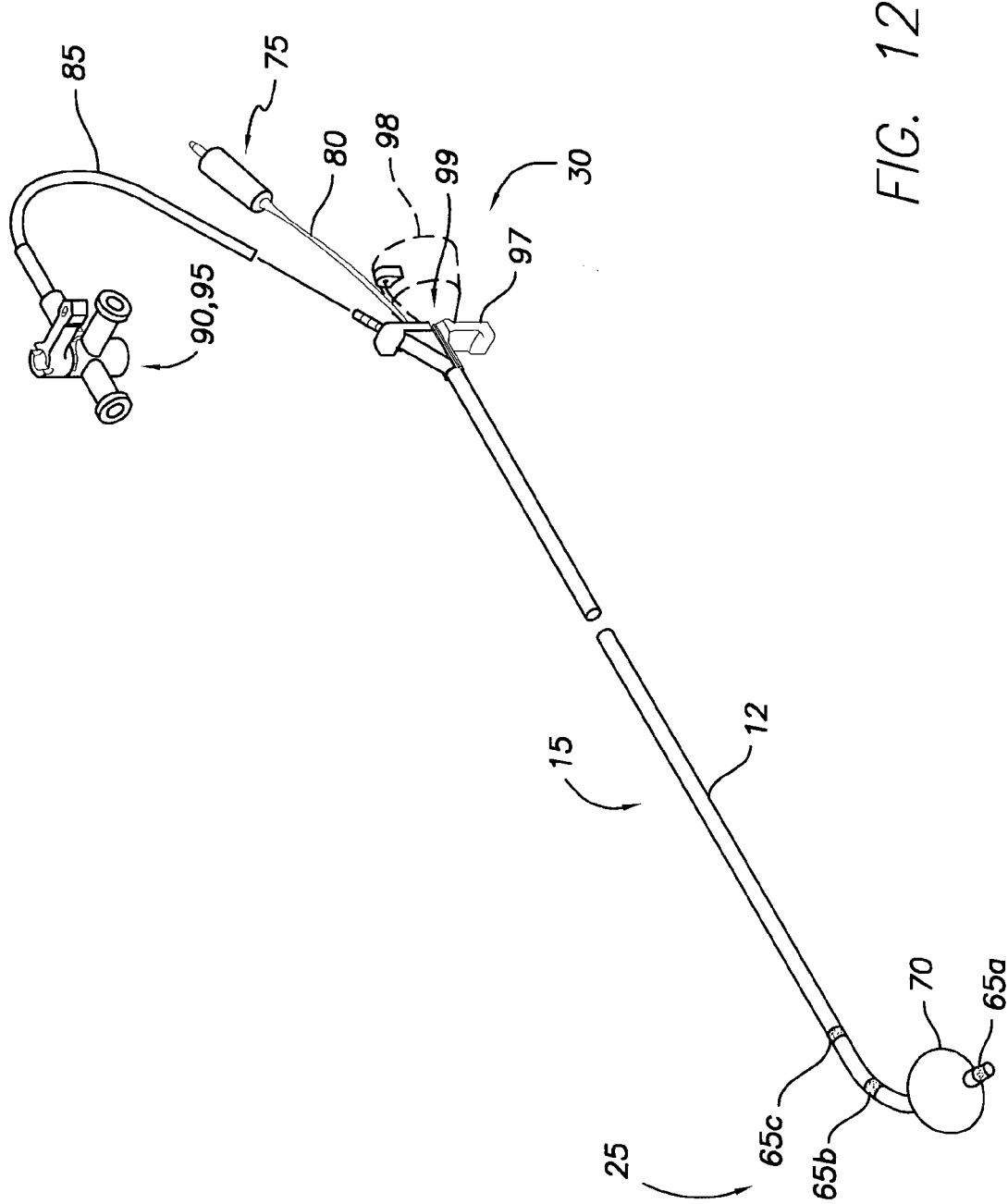
FIG. 12 is an isometric view of another embodiment of the delivery tool, wherein the tool may or may not have a splittable body.

In some embodiments, a delivery tool 15 having some or all of the features discussed with respect to FIG. 2 may be configured as depicted in FIG. 12, which is an isometric view of such a delivery tool 15. As shown in FIG. 12, the distal end 25 of the delivery tool 15 may have multiple sensors 65 and an occlusion balloon 70. The proximal end 30 of the tool 15 may have an electrical connector 75, which may have connector pins or other types of connector configurations. The proximal end 30 of the tool 15 may also have a luer lock 90 and stop cock 95, which may be combined together in the form of a 3-way stopcock assembly. The proximal end 30 of the tool 15 may also have a receiving end 97 adapted to receive and couple with a hemostasis valve 98 (shown in phantom lines).

The tool tubular body 12 may be adapted to split or slit via a score line or other means of creating a longitudinally extending stress concentration in the body 12. The receiving end 97 may be configured to split via a score 99 or similar stress-creating mechanism to cause the end 97 to split, thereby facilitating the splitting of the body 12. In some embodiments, the sensors 65 and balloons 70 will also be adapted to split or slit in a manner similar to the body 12. In some embodiments, the tool 15 will have those additional features discussed with respect to FIG. 9, including additional balloons 70, etc.

Figure 3:
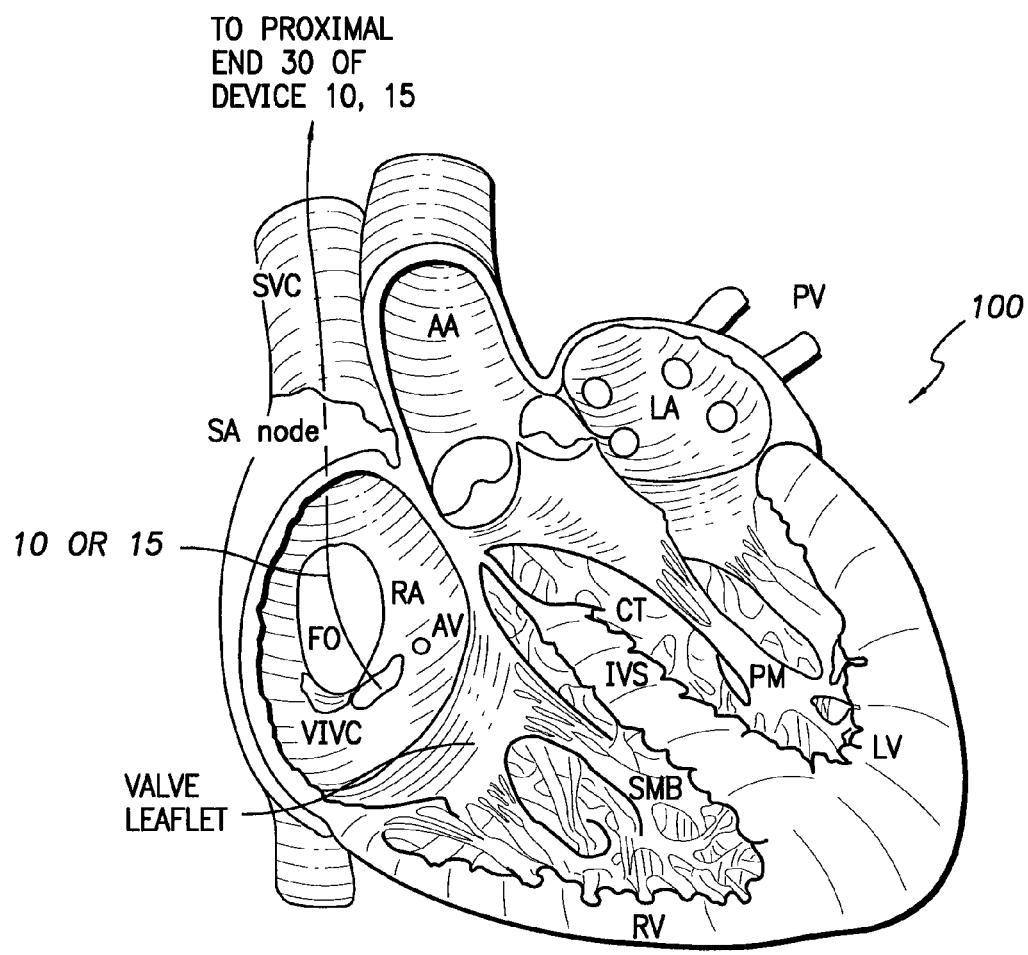
FIG. 3 is a partially cut open anterior view of a heart wherein a device extends through the superior vena cava and the coronary sinus ostium and into the coronary sinus.
Figure 4:
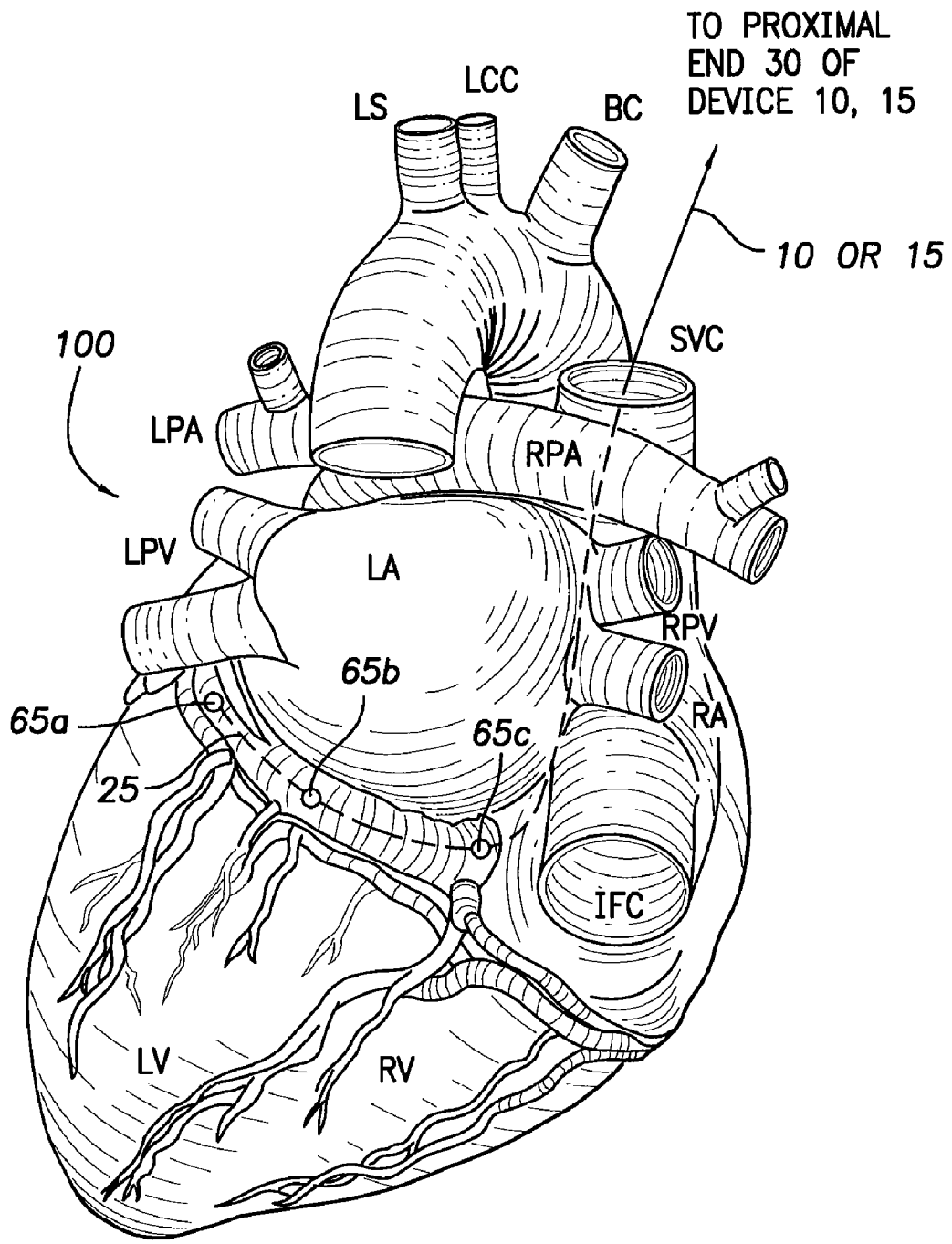
FIG. 4 is a posterior view of the heart and a distal segment of the device extending through the coronary sinus and into the great cardiac vein.

For a discussion of a method of employing either of the above-discussed devices 10, 15 to optimize CRT, reference is made to FIGS. 3 and 4. FIG. 3 is a partially cut open anterior view of a heart 100 wherein a device 10, 15 extends through the superior vena cava ("SVC") and the CS ostium and into the CS. FIG. 4 is a posterior view of the heart 100 and a distal segment of the device 10, 15 extending through the CS and into the great cardiac vein.

As shown in FIG. 4, the distal segment of the device, whether the device is the lead 10 of FIG. 1 or the delivery tool 15 of FIG. 2, is positioned in the CS such that the distal sensor 65a is located in the great cardiac vein, the intermediate sensor 65b is located in the middle portion of the CS, and the proximal sensor 65c is located near the CS ostium. In such a placement of the sensors 65 within the CS and associated coronary venous anatomy, the resulting pressure readings from the sensors 65 may appear as depicted in FIG. 5, which is a graphical comparison of the three sensor readings to LV pressure.

CS pressure and its waveform are a function of a number of components. Two main components of CS pressure include right atrial pressure ("RAP"), which is a function of the RA pressure pulse, and left ventricle pressure ("LVP"), which is a function of the LV contractile pressure pulse. Accordingly, analysis of the atrial and ventricular components of CS pressure can be used to derive a number of parameters for CRT lead placement and timing optimization, including but not limited to maximum pressure, rate of change of pressure (dP/dt), and duration and timing of the pre-ejection period. Additionally, analysis of the atrial and ventricular components of CS pressure can be used to assess changes in pressure pulse width, maxima, minima, peak-to-peak amplitude, dP/dt amplitude, $dP/dt_{max}$ and timing to evaluate intra-ventricular and inter-ventricular contraction. Also, analysis of the atrial and ventricular components of CS pressure allows for atrio-ventricular timing interval optimization by evaluating atrial peak amplitude, maxima, minima, and dP/dt. The timing of the atrial component and the ventricular component in relation to each other can be analyzed. Any of the pressure parameters can be analyzed in conjunction with electrical data (from IEGM or ECG) to assess electromechanical function.

Figure 5:
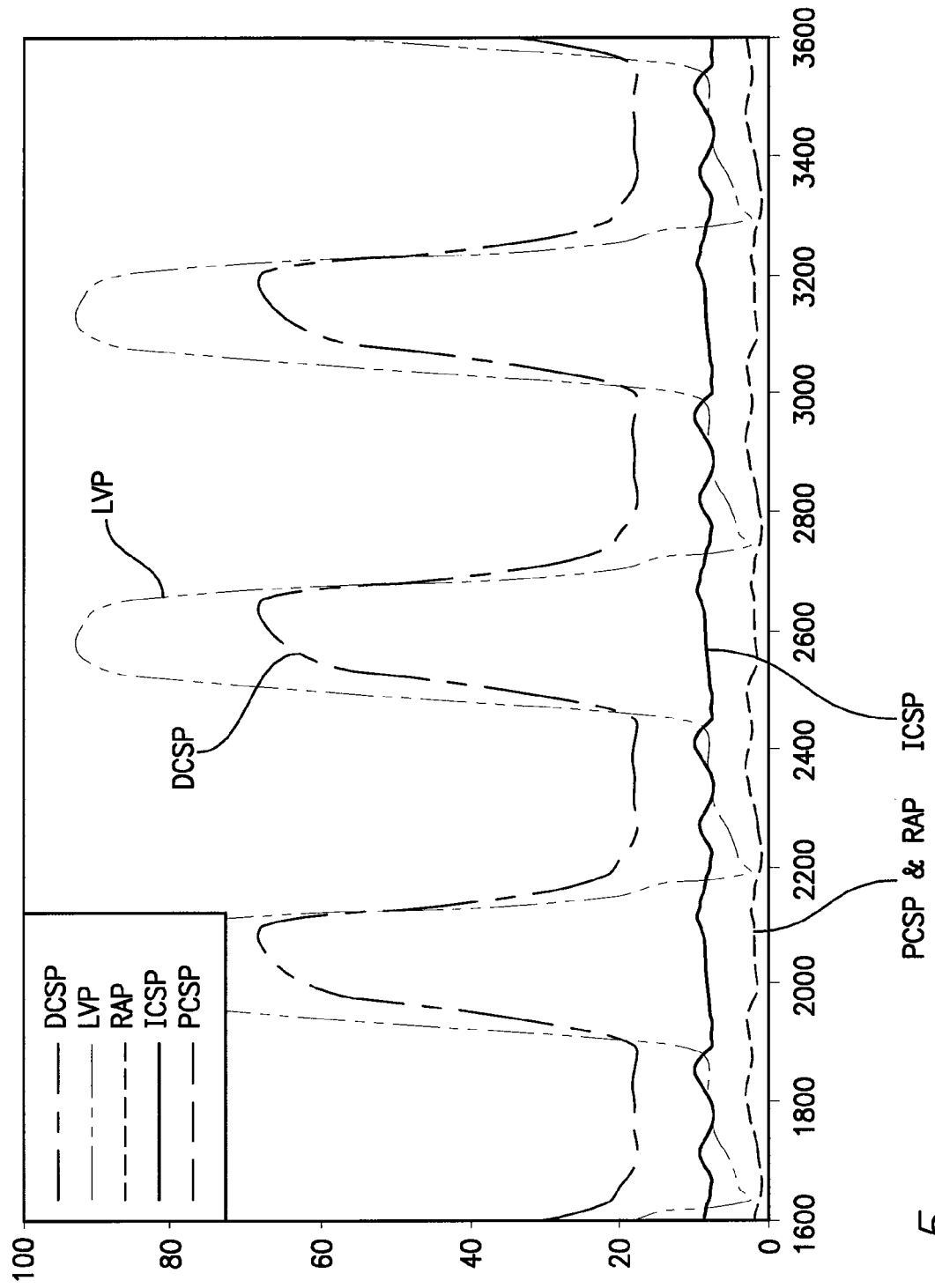
FIG. 5 is a graphical comparison of the three sensor readings to left ventricle pressure.

As can be understood from FIG. 5, the portion of the CS pressure attributable to LVP is more prevalent in the distal venous structure and less prevalent (although observable) near the CS ostium. Thus, the distal CS pressure reading ("DCSP") in FIG. 5, which is provided by the distal sensor 65a in the great cardiac vein in FIG. 4, generally corresponds to LVP.

As can be understood from FIG. 5, the portion of the CS pressure attributable to RAP is more predominant near the CS ostium and less prevalent in the distal venous anatomy. Thus, the proximal CS pressure reading ("PCSP") in FIG. 5, which is provided by the proximal sensor 65c near the CS ostium in FIG. 4, is essentially identical to RAP in FIG. 5.

For un-occluded sensors, the timing (with respect to the P wave portion of the ECG signal) of the right atrial ("RA")

component of the CS pressure pulse varies depending on the location of the sensor within the coronary sinus. As the sensor is moved further distal into the coronary sinus, the RA component of the CS pressure pulse decreases and the time between the P wave portion of the ECG signal and the RA component increases. This is due to the increased time it takes for the RA pressure wave to travel down the CS.

The intermediate CS pressure reading ("ICSP") in FIG. 5, which is provided by the intermediate sensor 65*b* in the intermediate portion of the CS in FIG. 4, provides the pressure of the intermediate portion of the CS. Depending on the location within the coronary sinus, the waveform for the ICSP can show overlapping elements of both right atrial and left ventricular pressure pulses.

Figure 6:
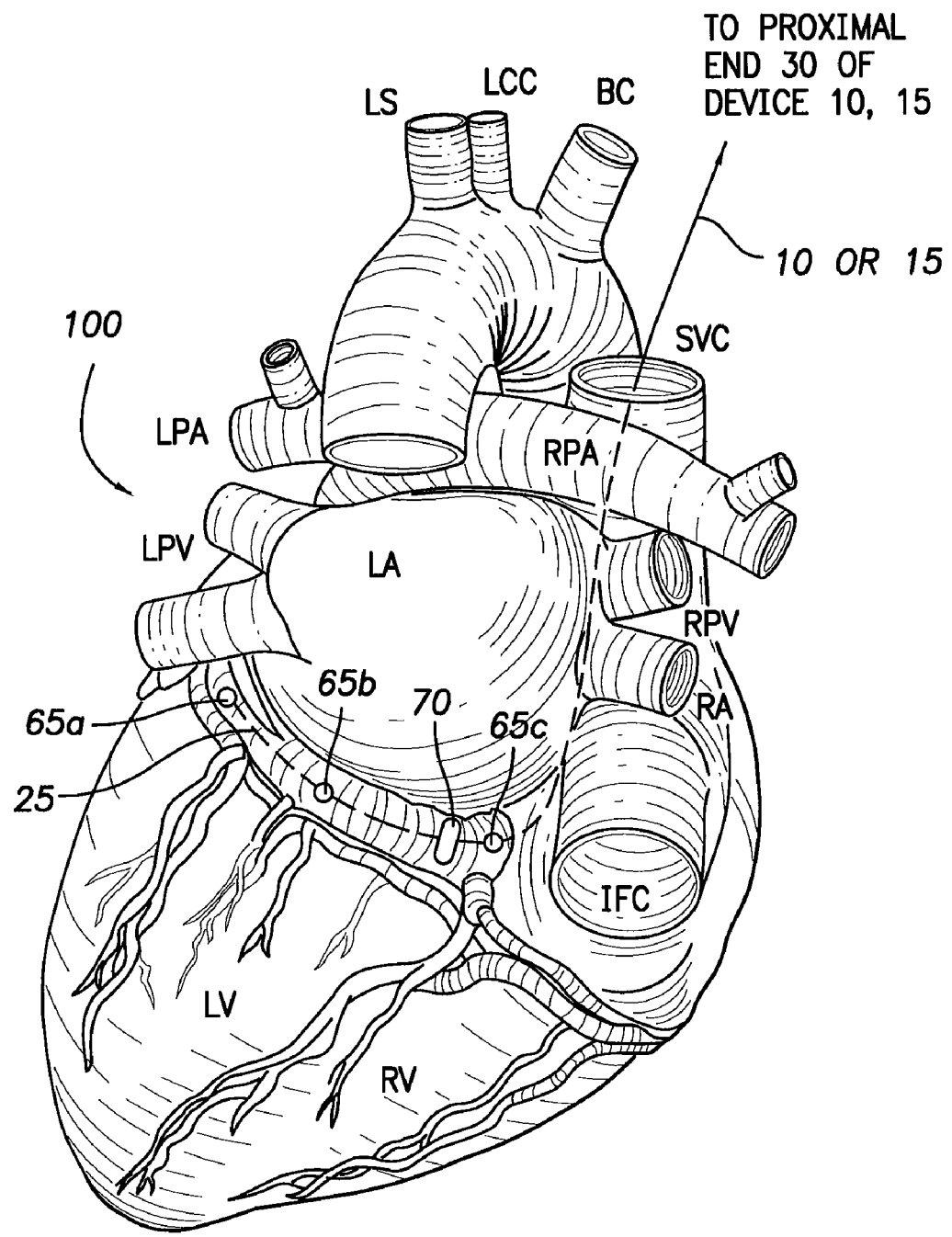
FIG. 6 is the same view depicted in FIG. 4, except a balloon of the lead of FIG. 1 or the tool of FIG. 2 is inflated just distal of the most proximal sensor.
Figure 7:
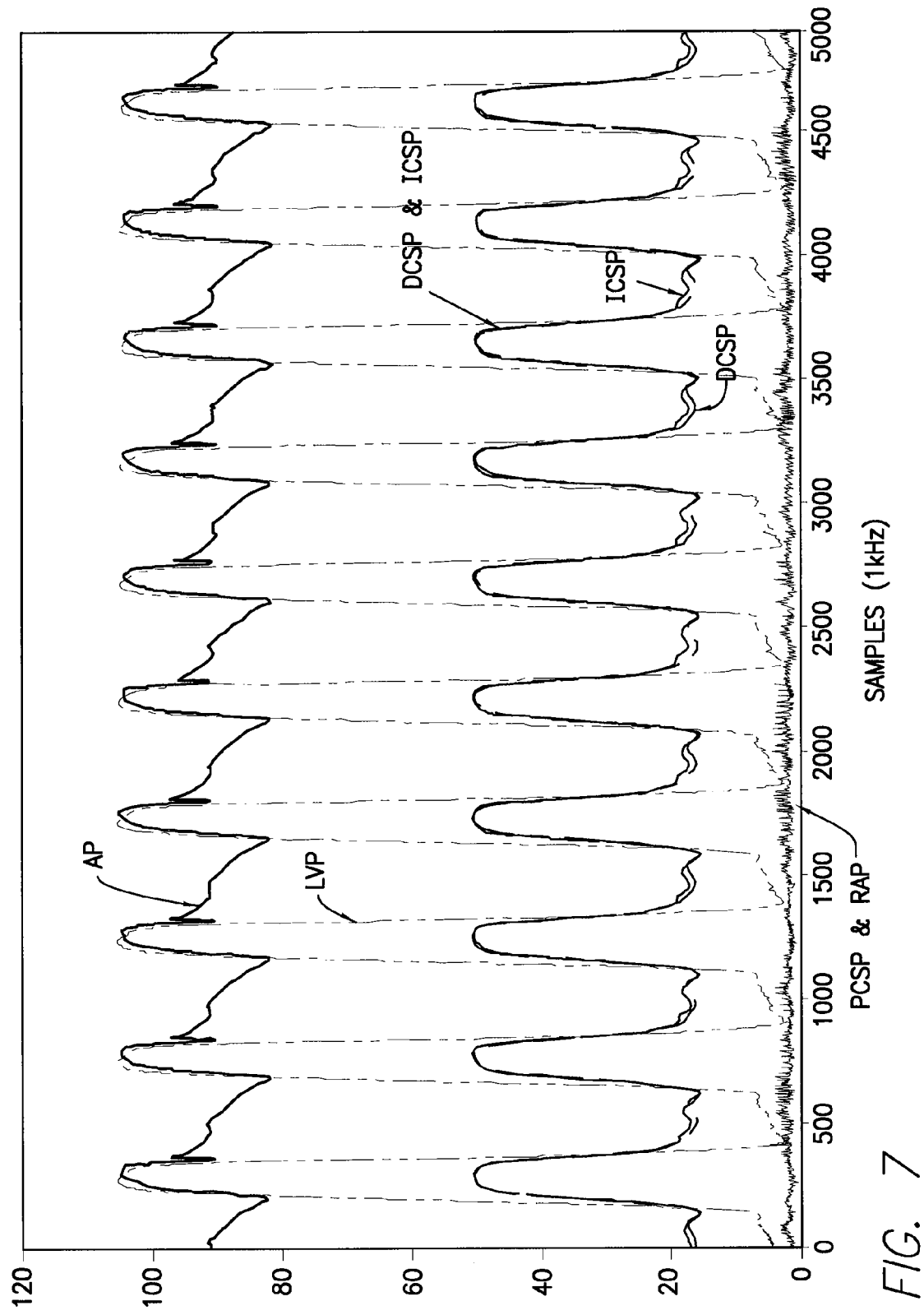
FIG. 7 is a graphical comparison of the three sensor readings to left ventricle pressure and aortic pressure when the coronary sinus is occluded by the balloon as depicted in FIG. 6.

As indicated in FIG. 6, which is the same view depicted in FIG. 4, a balloon 70 of the lead 10 of FIG. 1 or the tool 15 of FIG. 2 is inflated. The balloon 70 is just distal of the proximal sensor 65*c* and, when inflated, occludes the CS. Occluding the CS in such a manner captures the volume of blood in the venous circulation and isolates the RAP portion of the CS pressure from the rest of portions constituting the ventricular pressure pulse. Thus, occluding the CS prevents blood from draining into the right atrium. Accordingly, as can be understood from FIG. 7, which is a graphical comparison of the three sensor readings to LVP and aortic pressure ("AP") when the CS is occluded by the balloon 70 as depicted in FIG. 6, all sensors distal to the occlusion are nearly identical to each other and generally correspond with LVP. Accordingly, occluding the CS as depicted in FIG. 6 to isolate the proximal sensor 65*c* from the other two sensors 65*a*, 65*b* provides a an accurate representation of LVP and contractility (dP/dt) via the readings from the sensors 65*a* and 65*b*.

Figure 8:
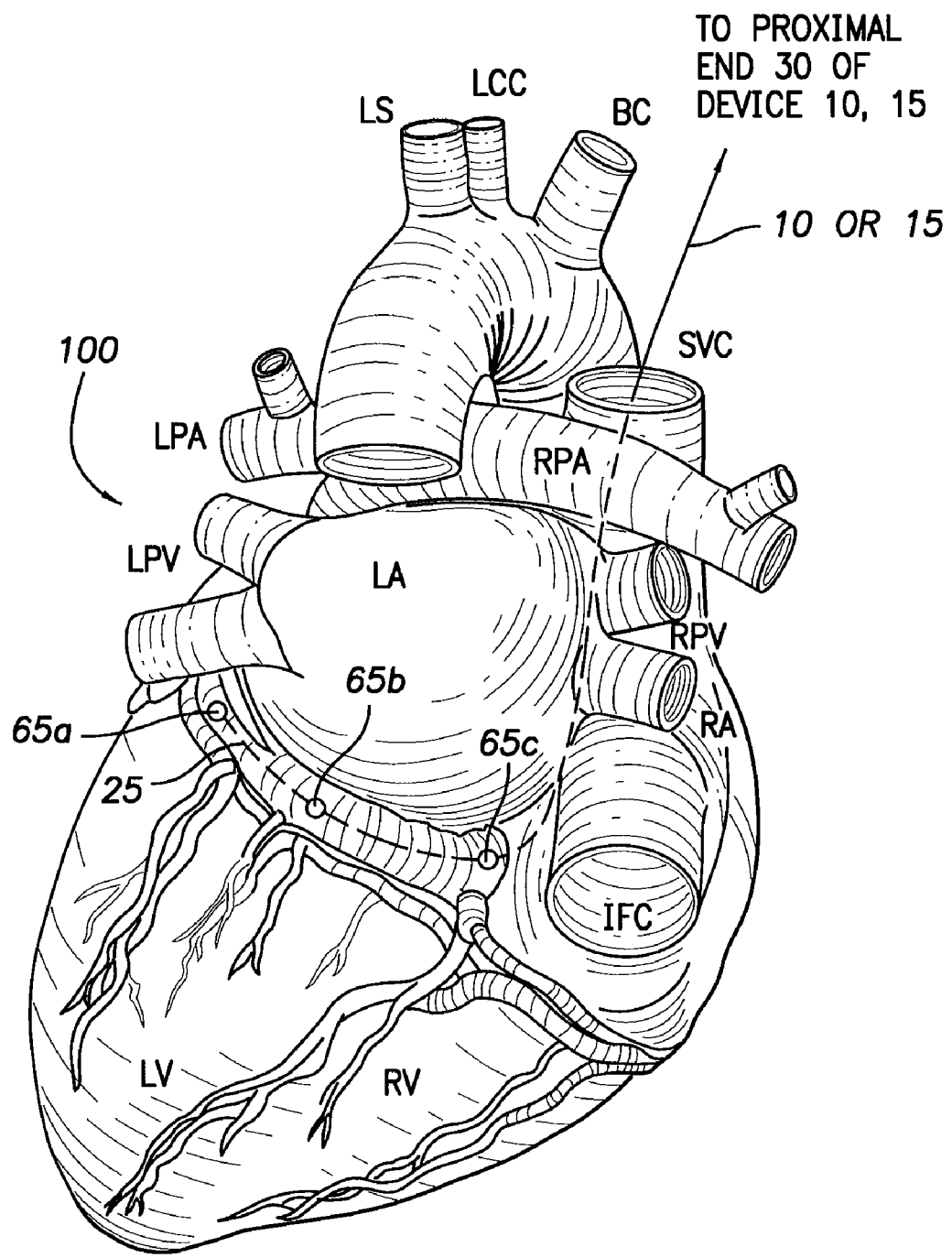
FIG. 8 is the same view depicted in FIG. 4 with the lead of FIG. 1 or the tool of FIG. 2 being employed.

The devices 10, 15 and methods disclosed herein may be used to assess ventricular dyssynchrony by taking pressure measurements associated with different coronary veins (e.g., great, middle, lateral and small cardiac veins) and comparing a dyssynchronous pressure pulse to a known synchronous pressure pulse. A pressure reading for a specific coronary vein may be taken when a sensor 65 is within the specific coronary vein or in close proximity to the junction between the specific vein and the CS. For example, as depicted in FIG. 8, which is the same view depicted in FIG. 4 with the lead 10 of FIG. 1 or the tool 15 of FIG. 2 being employed, a pressure reading associated with the great cardiac vein is taken by the distal sensor 65*a* when located in the great cardiac vein. Similarly, the intermediate sensor 65*b* and proximal sensor 65*c* respectively take pressure readings associated with the lateral cardiac vein and the middle cardiac vein when the sensors 65*b*, 65*c* pass by or are located at the junction between the CS and the specific cardiac vein. Any of these measured pressure pulses that are dyssynchronous can be compared to pressure pulses that are synchronous.

Figure 9:
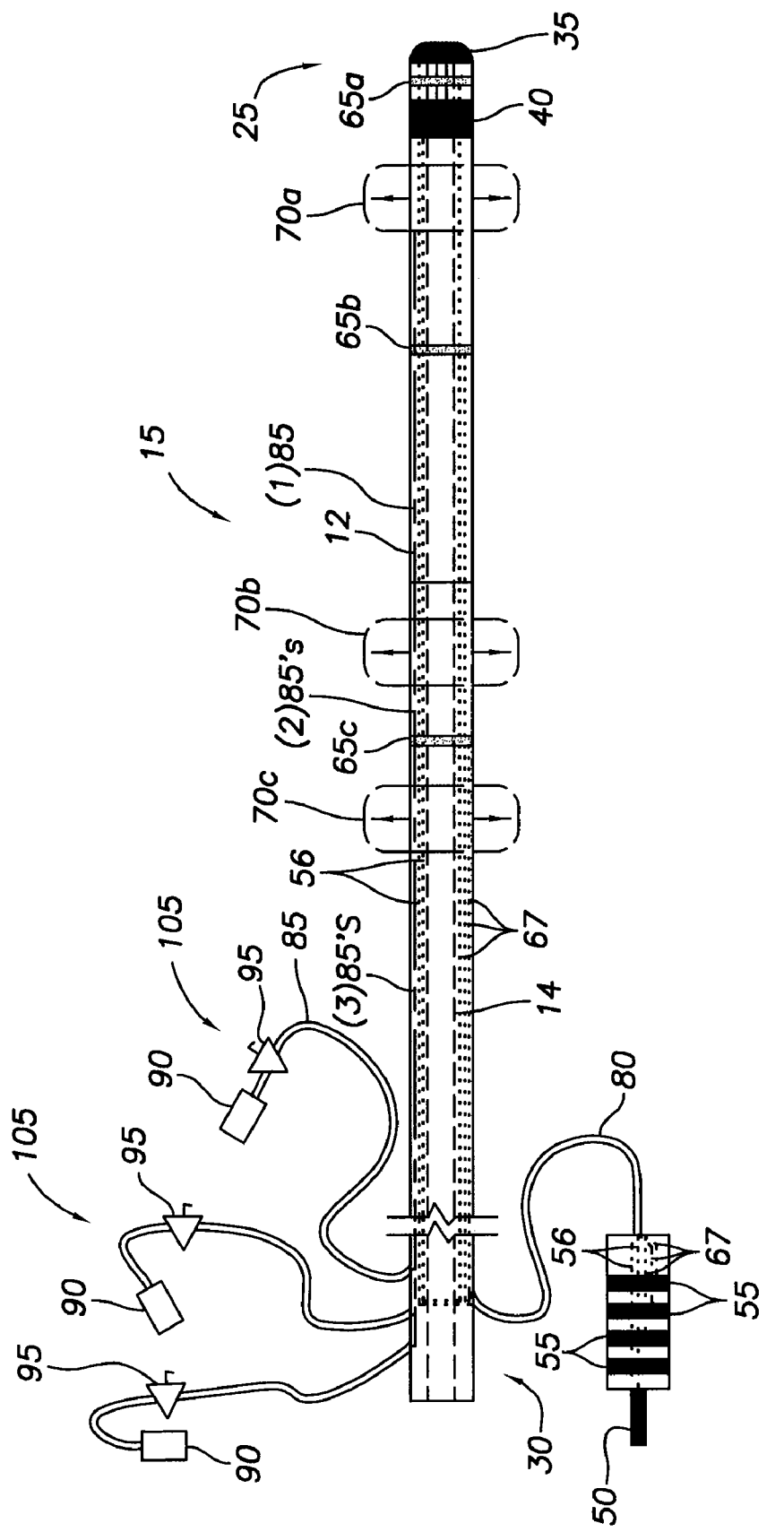
FIG. 9 is the same view as FIG. 2, except the tool has multiple balloons.
Figure 10:
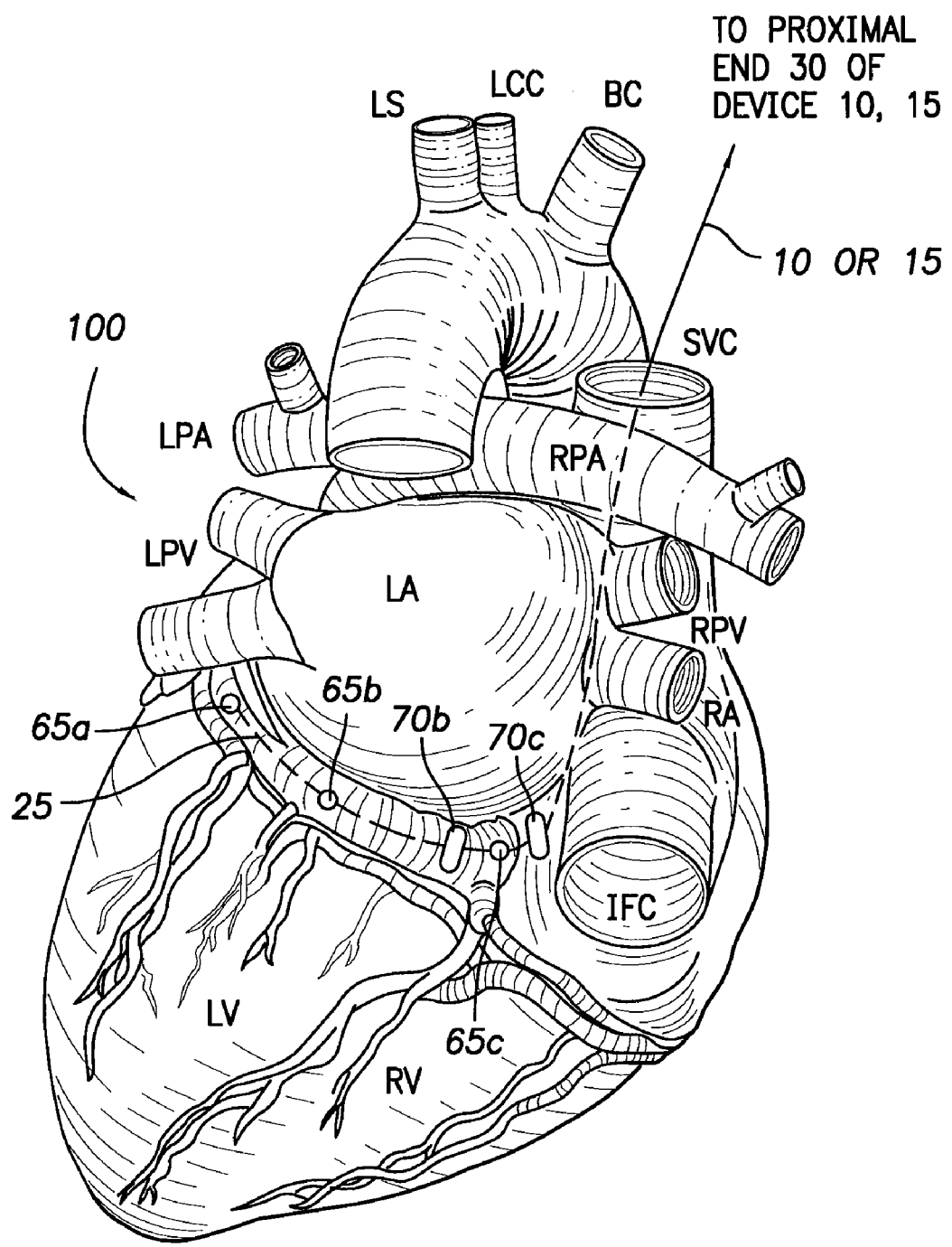
FIG. 10 is the same view as FIG. 6, except with multiple balloons inflated.
Figure 11:
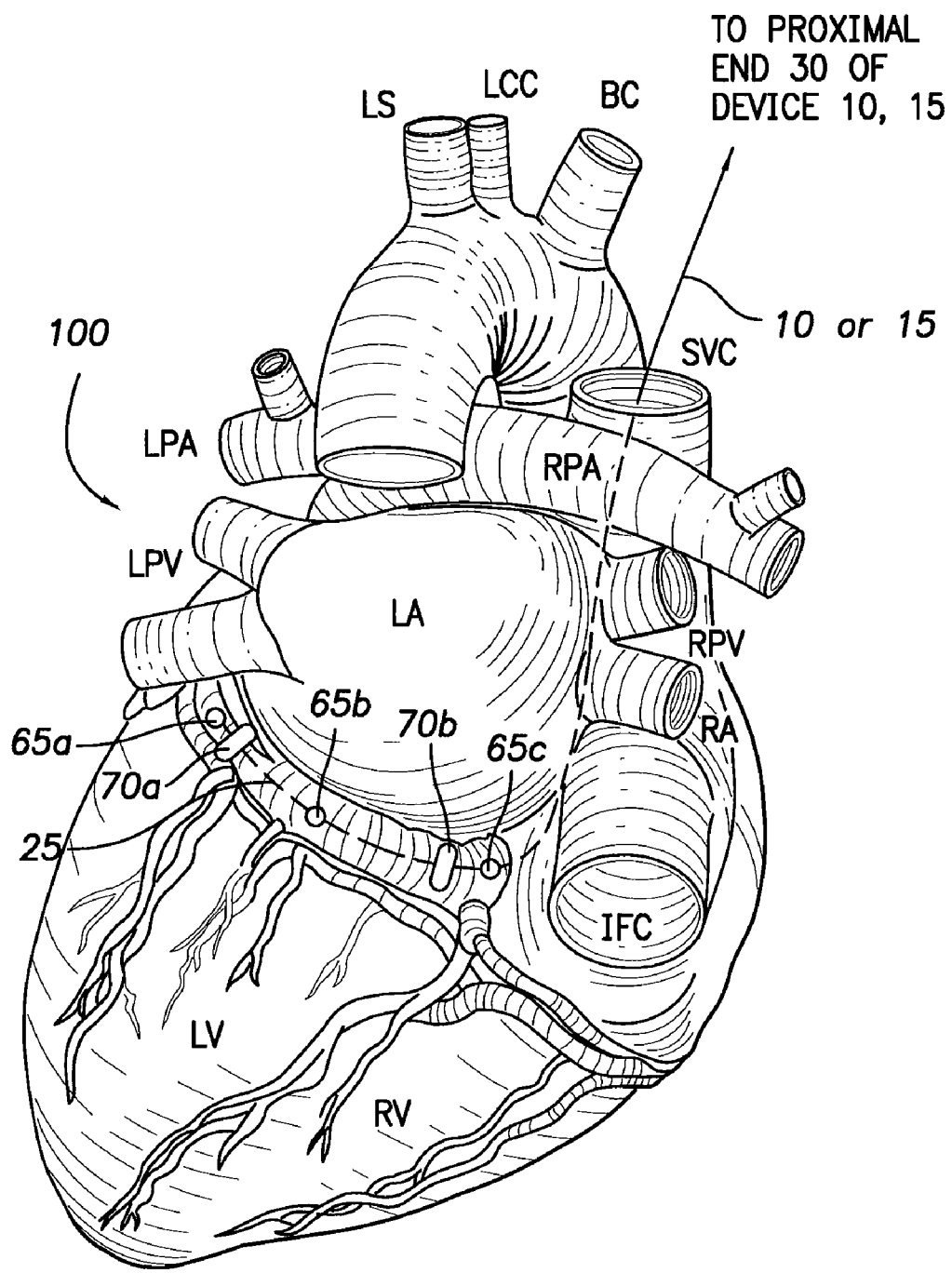
FIG. 11 is the same view as FIG. 10, except with a different combination of multiple balloons inflated.

A pressure reading for a specific coronary vein may be taken when a sensor 65 is in isolated communication with specific coronary vein. A discussion of such a process is now provided with respect to FIGS. 9-11. FIG. 9 is the same view as FIG. 2, except the tool has multiple balloons 70. FIGS. 10 and 11 are the same as FIG. 6, except with different combinations of balloons inflated.

As indicated in FIG. 9, a delivery tool 15 may be provided with multiple balloons 70 and multiple inflation lumen configurations 105 for independently inflating each balloon 70. Specifically, in one embodiment, the tool 15 includes a distal balloon 70*a* just proximal of the distal sensor 65*a*, an intermediate balloon 70*b* just distal of the proximal sensor 65*c*, and a proximal balloon 70*c* just proximal of the proximal sensor 65*c*. In other embodiments, the tool 15 will have a greater or lesser number of balloons 70 and/or the balloons 70 will be located differently with respect to spacing and/or location. While FIG. 9 depicts a tool 15, it should be understood that the multiple balloon configurations discussed herein can be readily applied to a lead 10.

Each inflation lumen configuration 105 will include a luer lock 90, a stop valve 95, and a dedicated lumen 85 extending from the respective luer lock 90 to the respective balloon 70. As a result, the balloons 70*a*, 70*b*, 70*c* will be independently inflatable relative to each other. In other embodiments, one or more of the balloons 70*a*, 70*b*, 70*c* will be ganged together to be served by a single lumen 85 such that the balloons will not be independently inflatable.

As shown in FIG. 10, the proximal sensor 65*c* can be located near a junction between the CS and, for example, the middle coronary vein. The intermediate and proximal balloons 70*b*, 70*c* can be inflated to isolate the proximal sensor 65*c* from generally all pressure influences, except the pressure of the middle coronary vein. Thus, the proximal sensor 65*c* will read the pressure of the middle coronary vein.

As shown in FIG. 11, the distal sensor 65*a* is located in the great cardiac vein, the intermediate sensor 65*b* is located generally midway in the CS, and the proximal sensor 65*c* is located near the intersection of the CS with the middle coronary vein. The distal and intermediate balloons 70*a*, 70*b* can be inflated. As a result, the distal sensor 65*a* is generally isolated from all pressure influences, except the pressure of the great cardiac vein. Also, the intermediate sensor 65*b* is generally isolated from all pressure influences, except the pressure of the posterior vein or the left marginal vein. Thus, the distal sensor 65*a* will read the pressure of the great coronary vein and the intermediate sensor 65*b* will read the pressure of the posterior vein or the left marginal vein.

The isolated pressure information obtained via the actions taken in FIGS. 10 and 11 can be used in a manner similar to that explained with respect to FIG. 8. For example, any of these measured isolated pressure pulses that are dyssynchronous can be compared to pressure pulses that are synchronous.

The above-described lead 10 and/or delivery tool 15 may be used for CRT optimization. For a discussion of a method optimizing CRT employing the above-described delivery tool 15, reference is made to FIG. 13, which is a diagram outlining the method.

Figure 13:
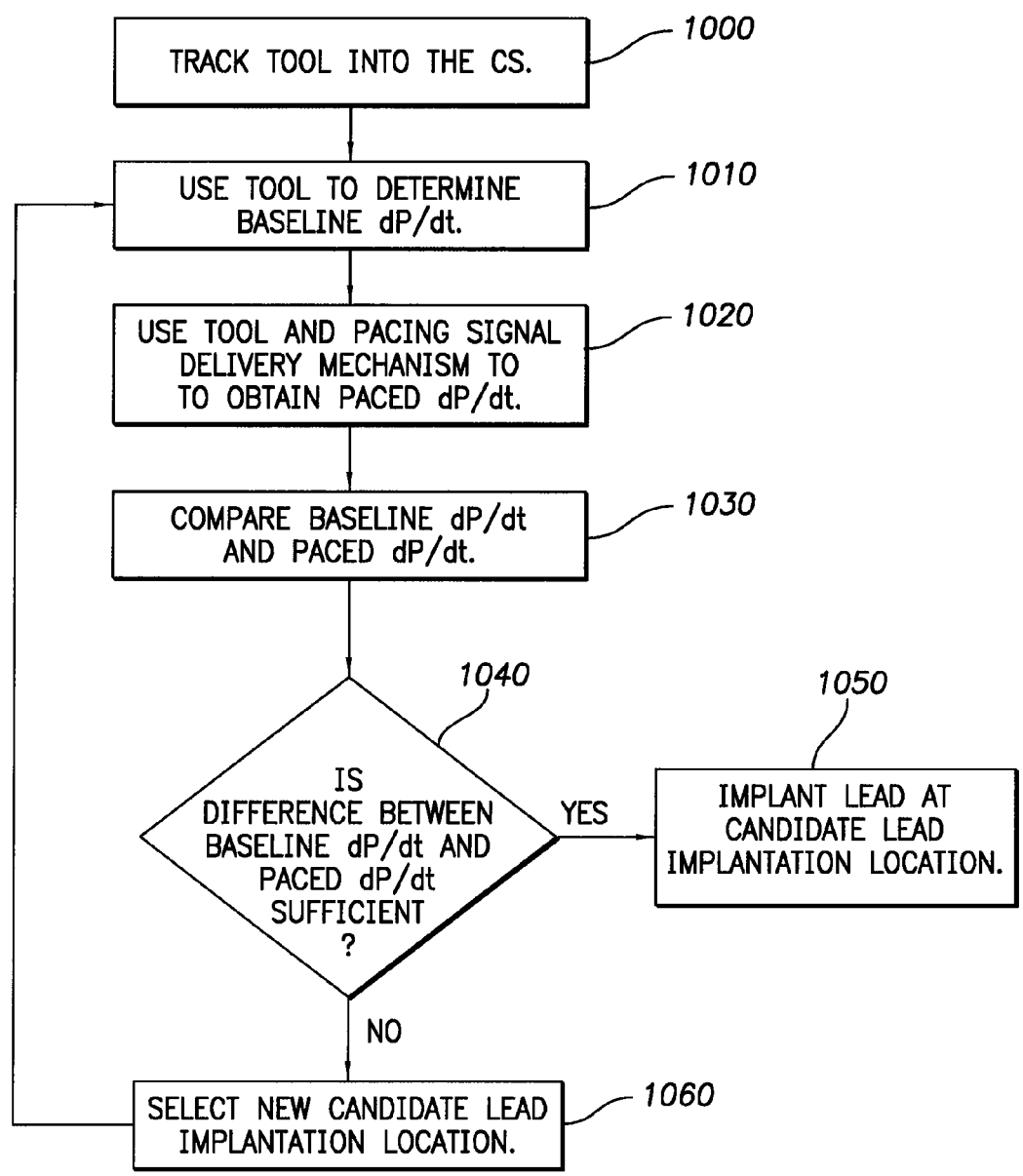
FIG. 13 is a diagram outline a method of employing a delivery tool to optimize CRT.

As indicated in FIG. 13, the tool 15 is tracked into the CS [block 1000]. In one embodiment, a lead to be implanted via the tool 15 may be tracked through the tool to a candidate implantation location. Alternatively, in other embodiments, a guidewire or similar device is tracked through the tool instead of the lead, or no device at all is tracked through the tool at this point. The tool 15 is used to determine a baseline dP/dt [block 1010]. To obtain the baseline dP/dt, a balloon 70 on the tool 15 is inflated to occlude the CS and isolate the CS from the RA. Once the resulting CS pressure rise has stabilized, dP/dt is measured via a pressure sensor 65 on the tool 15 over the next few heart beats (e.g., 10 heart beats) and averaged (median could also be used) to obtain an average dP/dt for those heart beats. The balloon 70 is then deflated to eliminate the occlusion of the CS. The patient is then allowed to stabilize for approximately one to two minutes.

The tool 15 and a pacing signal delivery mechanism are then used to obtain a paced dP/dt [block 1020]. To obtain the paced dP/dt, the balloon 70 on the tool 15 is again inflated to occlude the CS and isolate the CS from the RA. Once the resulting CS pressure rise has stabilized, dP/dt is measured via a pressure sensor 65 on the tool 15 over the next few heart beats (e.g., 10 heartbeats) while the pacing signal delivery mechanism delivers a pacing signal to the candidate implantation location. The dP/dt measured over the paced heartbeats are averaged (median could also be used) to obtain an average dP/dt for those paced heartbeats. The balloon 70 is then deflated to eliminate the occlusion of the CS. The patient is then allowed to stabilize for approximately one to two minutes.

In one embodiment, the pacing signal delivery mechanism is a device that is tracked through the tool 15 to the candidate lead implantation location. In such an embodiment, the pacing signal delivery mechanism is the lead to be implanted or a guidewire or similar type of device configured to deliver a pacing signal to the candidate lead implantation location.

In another embodiment, the pacing signal delivery mechanism is an integral part of the delivery tool as depicted in FIG. 2 wherein the tool 15 includes conductors 67 and electrodes 35, 40. In such an embodiment, the delivery tool 15 is equipped to both deliver the pacing signal and measure dP/dt. Accordingly, no device needs to be tracked through the tool 15 for purposes of delivering the pacing signal to the candidate lead implantation location.

The baseline dP/dt and paced dP/dt are compared [block 1030]. If the difference between the baseline dP/dt and paced dP/dt is sufficient [block 1040], then the candidate lead implantation location is appropriate for lead implantation and the lead can then be implanted at the candidate lead implantation location [1050]. Where the pacing signal was delivered via a guidewire or the tool 15, the lead can then be tracked through the tool 15 for delivery to the lead implantation location. The lead is then implanted at the lead implantation location and the tool 15 is removed from about the lead via slitting or splitting.

Where the lead was already in the introducer and was the mechanism for delivering the pacing signal, the lead is then simply implanted at the lead implantation location. The tool 15 is then removed from about the lead via slitting or splitting.

If the difference between the baseline dP/dt and paced dP/dt is insufficient [block 1040], then a new candidate lead implantation location is selected [1060] and the above-described baseline and paced dP/dt measuring processes are repeated [i.e., return to block 1010] at the new candidate lead implantation location. If all possible candidate lead implantation locations are tested and none satisfy the required difference between the baseline dP/dt and paced dP/dt, then the lead implantation procedure is abandoned and the patient is identified as a non-responder to CRT.

In one embodiment, the procedure discussed with respect to FIG. 13 can be adapted to allow for the scouting-out of the lead implantation location that will allow CRT to be optimized. For example, the procedure described with respect to FIG. 13 can be repeated at a variety of candidate lead implantation locations to identify the implantation location corresponding to the greatest difference between baseline dP/dt and paced dP/dt. The lead can then be implanted at the identified implantation location, because in a large number of cases, the implant location having the greatest dP/dt differential between the baseline and paced conditions will provide the most optimized CRT.

Typically, the greater the dP/dt differential, the greater the contractility and the greater the likelihood CRT will be effective. In one embodiment, a patient will be identified as a responder to CRT if the paced dP/dt is at least 5% greater than the baseline dP/dt. Accordingly, the patient will be identified as a non-responder to CRT if the paced dP/dt is not greater than the baseline dP/dt.

While FIG. 13 and the immediately preceding discussion describe CRT optimization employing a delivery tool 15 that is the same as or similar to those depicted in FIGS. 2, 9 and 12, those skilled in the art will understand that a substantially similar, if not identical technique, may be employed using a lead 10 that is the same as or similar to that depicted in FIG. 1, wherein the lead is equipped with most, if not all of the following capabilities: pacing, pressure measuring, and occluding.

The above-mentioned methods and tools provide the physician with a mechanically derived hemodynamic index for CRT optimization. Also, by providing a lead 10 or introducer tool 15 in the CS and an additional lead 10 or introducer tool 15 in the RV, wherein the both the CS and RV devices 10, 15 have sensors 65, the pressure data from the RV device 10, 15 can be compared to the LV component of the CS device 10, 15 to optimize Bi-V interventions. The data from the pressure sensors can be used in combination with other St. Jude algorithms and optimizations, such as auto-capture, electronic repositioning, Automaticity™, and QuickOpt™. This could be done either in the pacer or in the programmer. In chronic applications, the pressure data could also be incorporated into remote monitoring applications, to monitor disease progression and response to therapy.

While the preceding discussion has been given with respect to the sensors 65 being pressure sensors, blood is an incompressible fluid. Accordingly, the sensors 65 could be velocity or flow sensors and the same type of correlations and predictions could be made using the flow or velocity of the blood, as opposed to its pressure. The pressure data may be used with other measured physiological properties, such as ventricular volume.

While the preceding discussion has been given with respect to sensors 65 being physically located on a distal portion or section of the lead or introducer tool, in some embodiments this will not be the case. For example, one or more or all of the sensors may be physically located at locations other than the distal portion or section of the lead or introducer tool. For example, the sensors may be physically located on a proximal portion or section of the lead or introducer tool. The sensors may be physically located inside the pacer as opposed to being located on the lead or introducer tool.

In any of these embodiments wherein the sensor is physically located at a place other than the distal portion or section of the lead or introducer tool, the sensor is still able to sense conditions at the distal portion or section. For example, a pressure sensor physically located at the proximal section or portion of the lead or introducer tool, or physically located in the pacer, may be placed in pressure sensing communication with conditions at the distal portion of the lead or introducer tool via a feature extending through the body of the lead or introducer tool. Such feature may be a fluid-filled column, which can be used with capacitive or piezo-based pressure sensors, or via fiber-optics if the sensor uses light waves to derive pressure.

Figure 15:
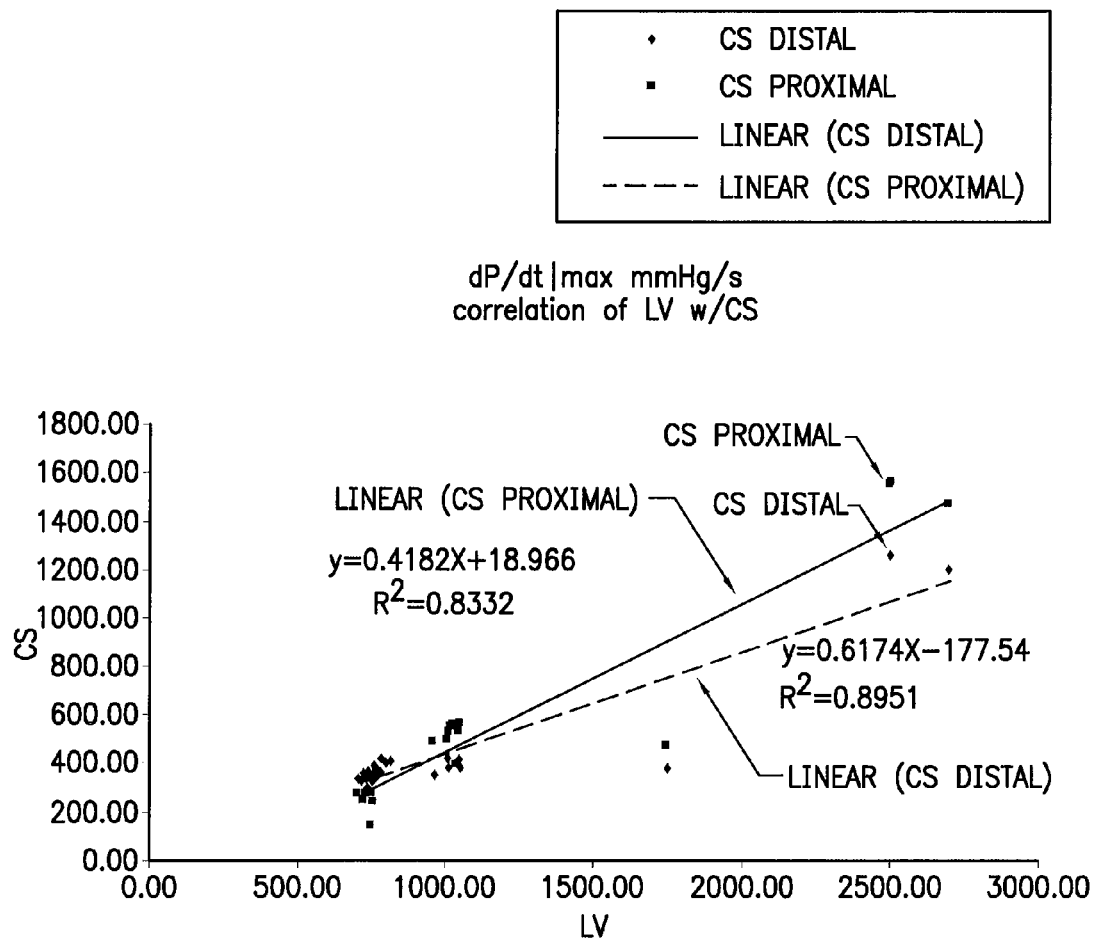
FIGS. 15-17 graphically indicate the correlation between signals obtained from the CS and LV.
Figure 16:
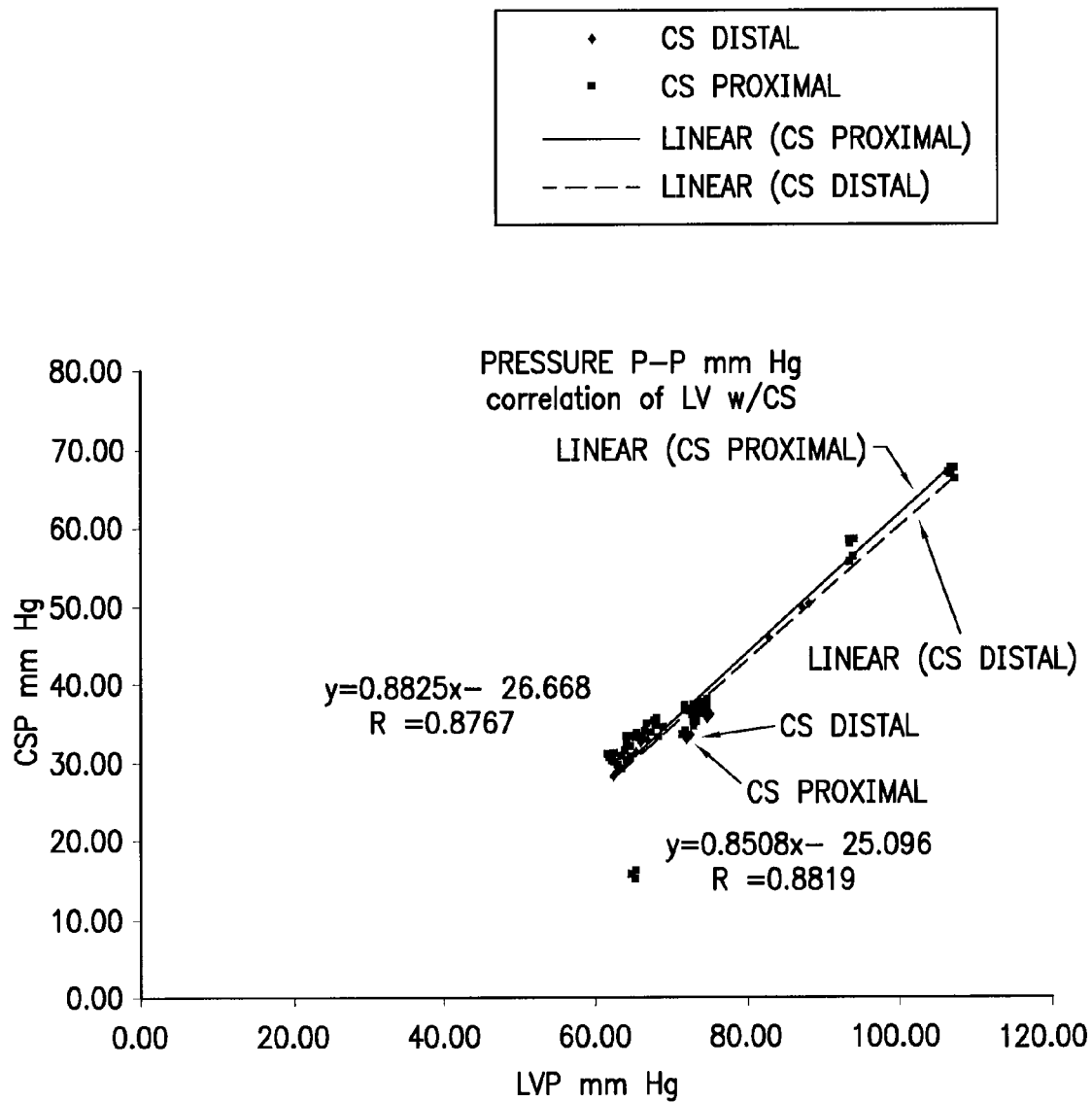
Figure 17:
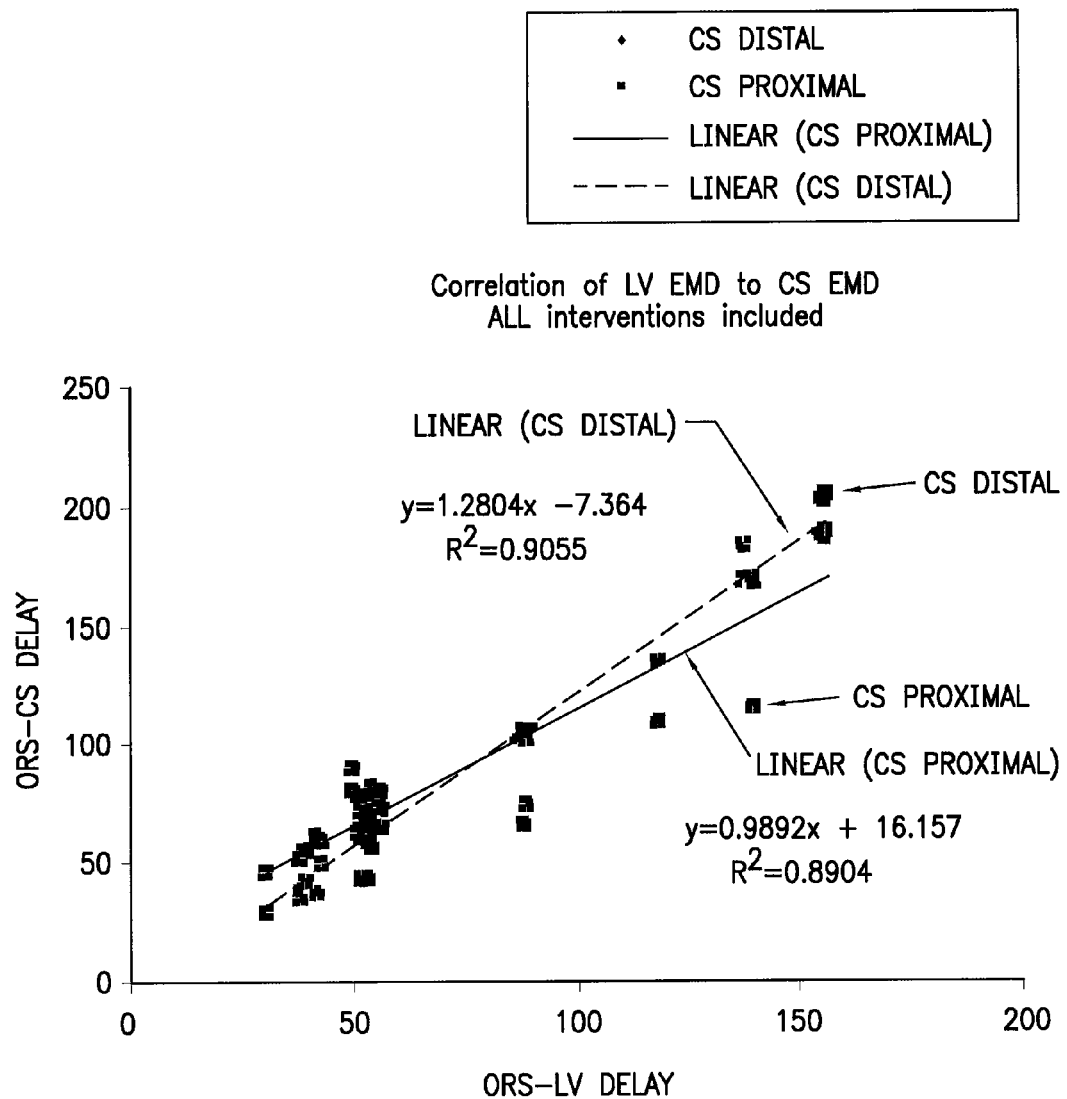
Figure 18:
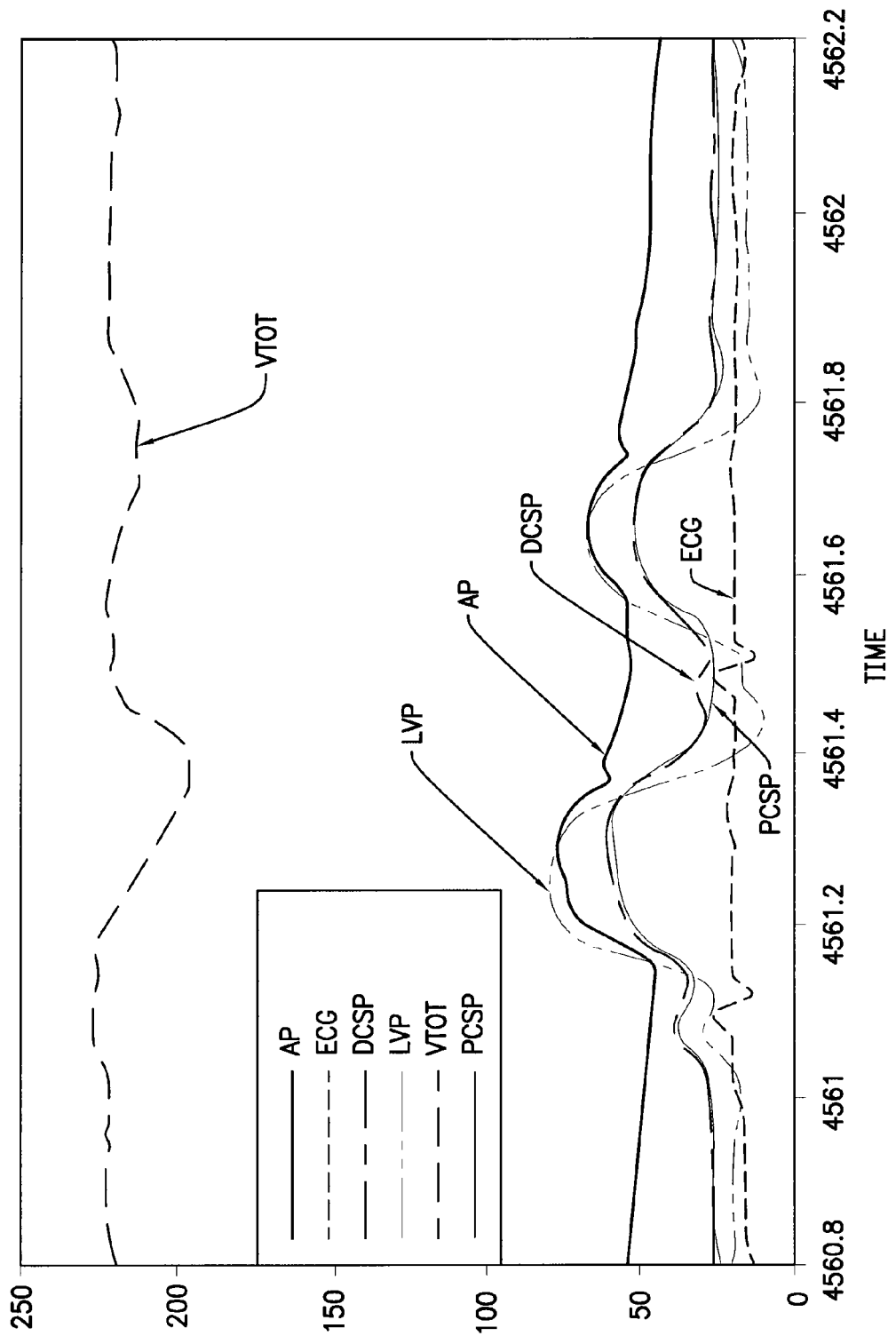
FIGS. 18-19 graphically compare distal coronary sinus pressure and proximal coronary sinus pressure to a variety of other readings.
Figure 19:
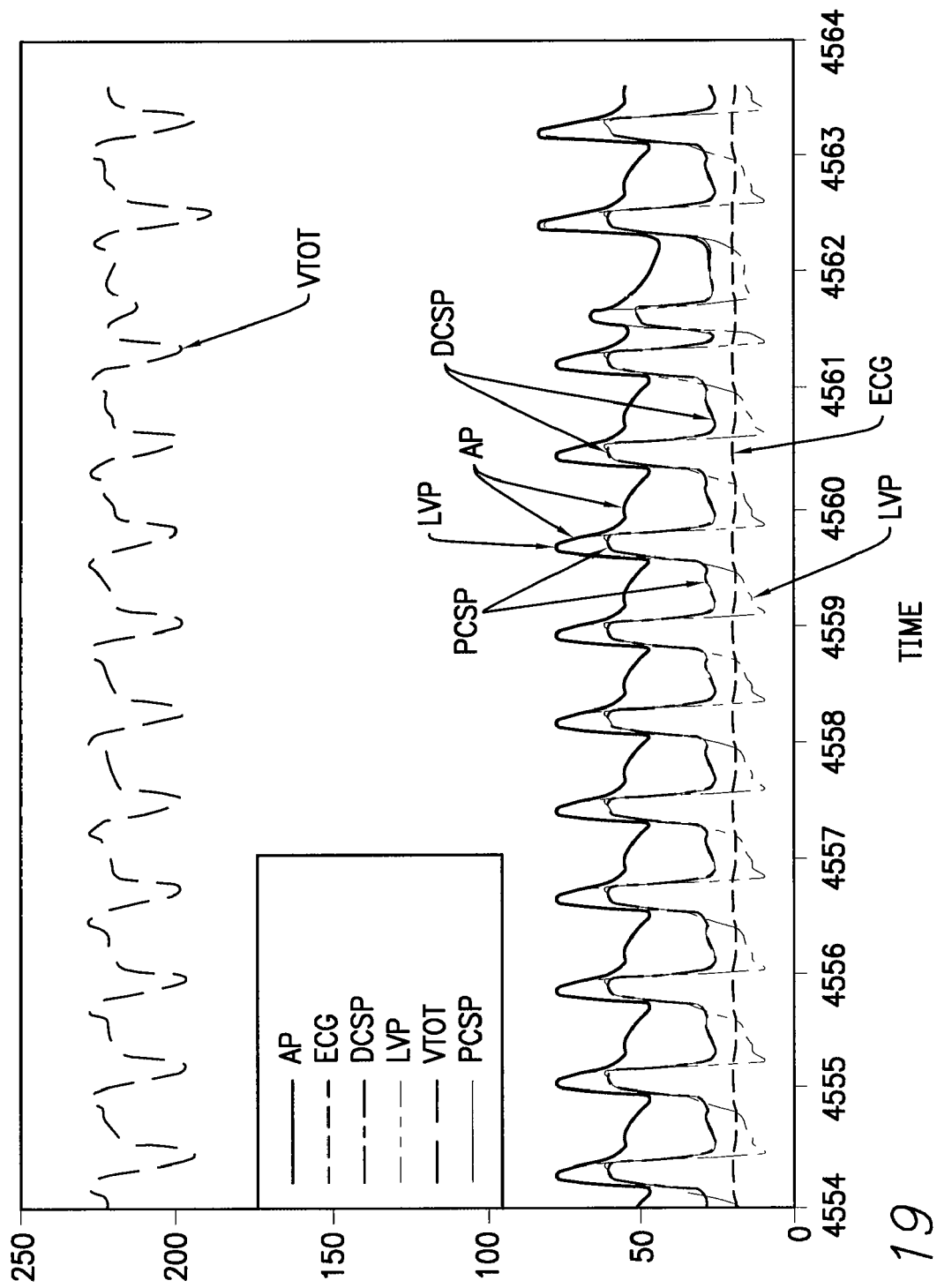
Figure 20:
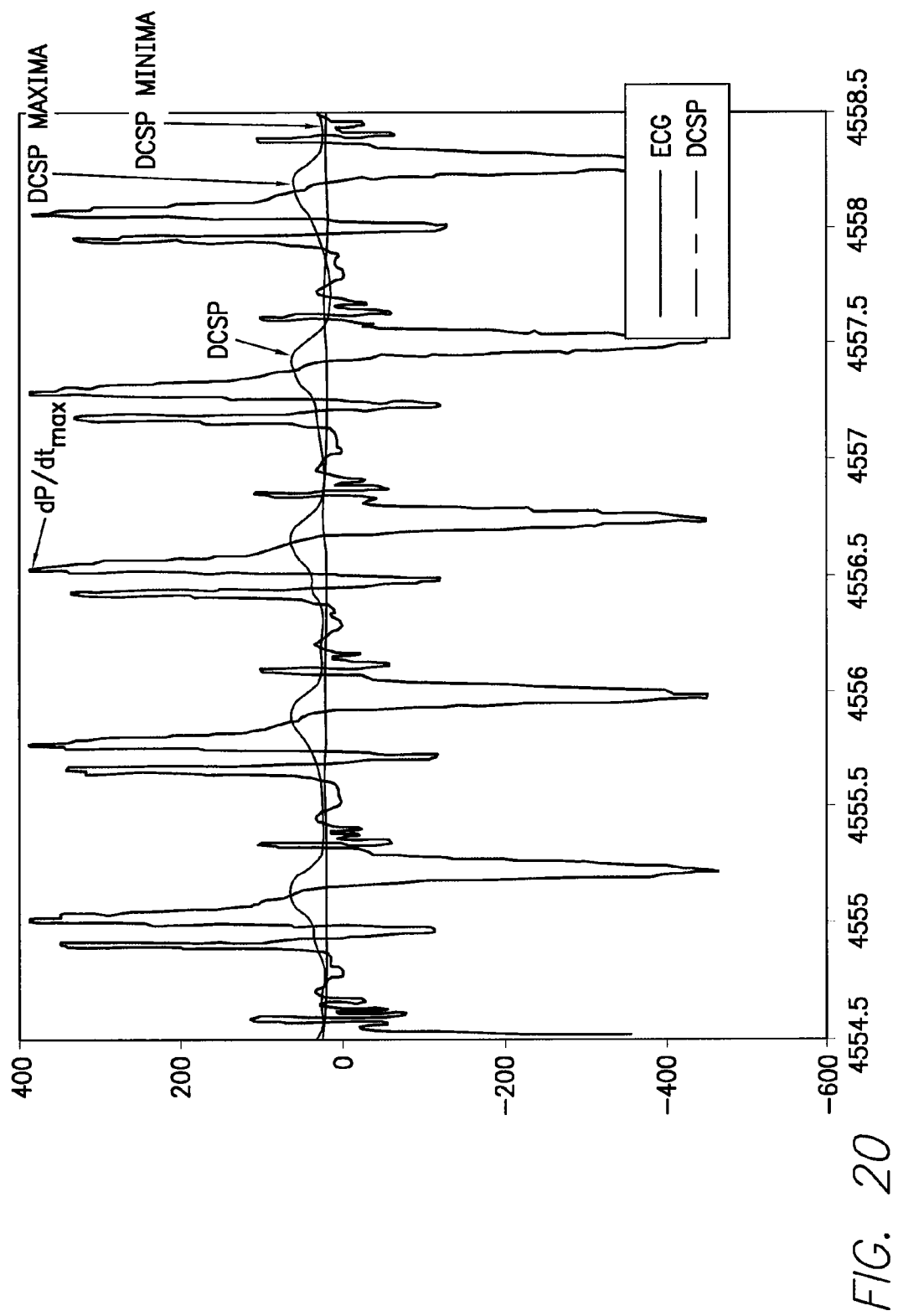
FIG. 20 graphically illustrates the selection of $dP/dt_{max}$ as determined from the distal coronary sinus pressure.

For a discussion of another embodiment of a method of determining data pertaining to left ventricular pressure ("LVP") and employing the data to optimize CRT, identify CRT non-responders, detect Afib, detect Vfib, optimize multi-site left ventricle pacing, optimize right ventricle lead placement and monitor or determine disease progression, reference is made to FIGS. 15-20. FIGS. 15-17 graphically indicate the correlation between signals obtained from the CS and LV. FIGS. 18-19 graphically compare distal coronary sinus pressure DCSP and proximal coronary sinus pressure PCSP to a variety of other readings. FIG. 20 graphically illustrates the selection of $dP/dt_{max}$ as determined from the DCSP.

LVP and LV dP/dt$_{max}$, which can serve as a contractility surrogate for performance of the LV, can be an excellent indicator for monitoring heart failure ("HF"). Because of the issues surrounding accessing the LV chamber to read LVP, it is necessary to find a surrogate for LVP. As discussed above, CS pressures measured from various locations in the coronary venous anatomy may be a good surrogate for LV performance.

In various experiments conducted at St. Jude Medical, Inc., primary locations where pressure was measured in the CS include the proximal region (e.g., in the CS approximately 2 cm from the CS ostium) and the distal region (e.g., approximately 5 cm from the CS ostium). Other pressure measurement locations within the CS and related vasculature include inside a coronary vein (e.g., mid lateral and great cardiac vein).

As discussed above, in the CS the use of an occlusive device may be advantageous to gather strong signals similar to the LV signal. However, deep in the CS anatomy and vasculature, even a non-occlusive signal was observed to have reasonable correlation with LV signals.

CS data obtained during the experimentation by St. Jude Medical, Inc. is graphically depicted in FIGS. 15-20 and will now be discussed. The experiments discussed with respect to FIGS. 15-20 were collected from a canine HF model.

The graphs of FIGS. 15-17 depict the correlation between the CS signal and the LV signal. Indices shown include CS pressure, dP/dt$_{max}$ and time to dP/dt$_{max}$ from the onset of QRS, which is associated with an electromechanical delay surrogate.

The graphs of FIGS. 18 and 19 illustrate the distal coronary sinus pressure ("DCSP") and proximal coronary sinus pressure ("PCSP") as respectively obtained from the distal and proximal regions of the CS after occluding the CS ostium. The left ventricular pressure ("LVP") and aortic pressure ("AP") were obtained for comparison from the LV chamber and descending aorta respectively. The electrocardiogram ("ECG") is also depicted.

The graph of FIG. 20 depicts the DCSP and the dP/dt$_{max}$ estimated from the DCSP. The ECG is also shown. The signals obtained from the CS region and depicted in FIG. 20 are similar to those depicted in FIGS. 18 and 19.

As can be understood from FIGS. 18-20, the coronary pressure signals track well with the LV signals and the aortic signals. Accordingly, the CS signals may be utilized as a surrogate for the LV signals. Therefore, the CS signals may be used to: monitor disease progression; optimize CRT, multi-site LV pacing and RV lead placement; and detect Afib and Vfib.

As can be understood from FIG. 20, peak CS pressure values can be selected and correlated with LV pressures. For example, a minima, maxima and maxima-minima (pressure range) may be selected for a measured CS pressure. As shown in FIG. 20, in one embodiment, the minima and maxima pressure is identified off of the DCSP.

As can be seen in FIGS. 18 and 19, the CS signals precede the aortic signal by a 20-30 ms window. This indicates that the coronary pressure signal has an LV component in it, not just aortic or arterial. The 20-30 ms window makes the coronary sinus signal useful in calculating LV dP/dt$_{max}$ (see FIG. 20), may serve as a surrogate for contractility of the heart. To be able to measure the contractility of the heart makes CS signal useful for optimizing CRT, identifying non-responders, detecting Afib, Vfib, disease progression or etc.

Another index that is useful is the time to dP/dt$_{max}$ from onset for the QRS portion of the ECG, or max contractility. As can be understood from FIG. 20, the time to dP/dt$_{max}$ is measured as the time from the QRS to the dP/dt$_{max}$. This index can be used in conjunction with dP/dt$_{max}$ so that maximum contractility and time to maximum contractility can be obtained.

Figure 21:
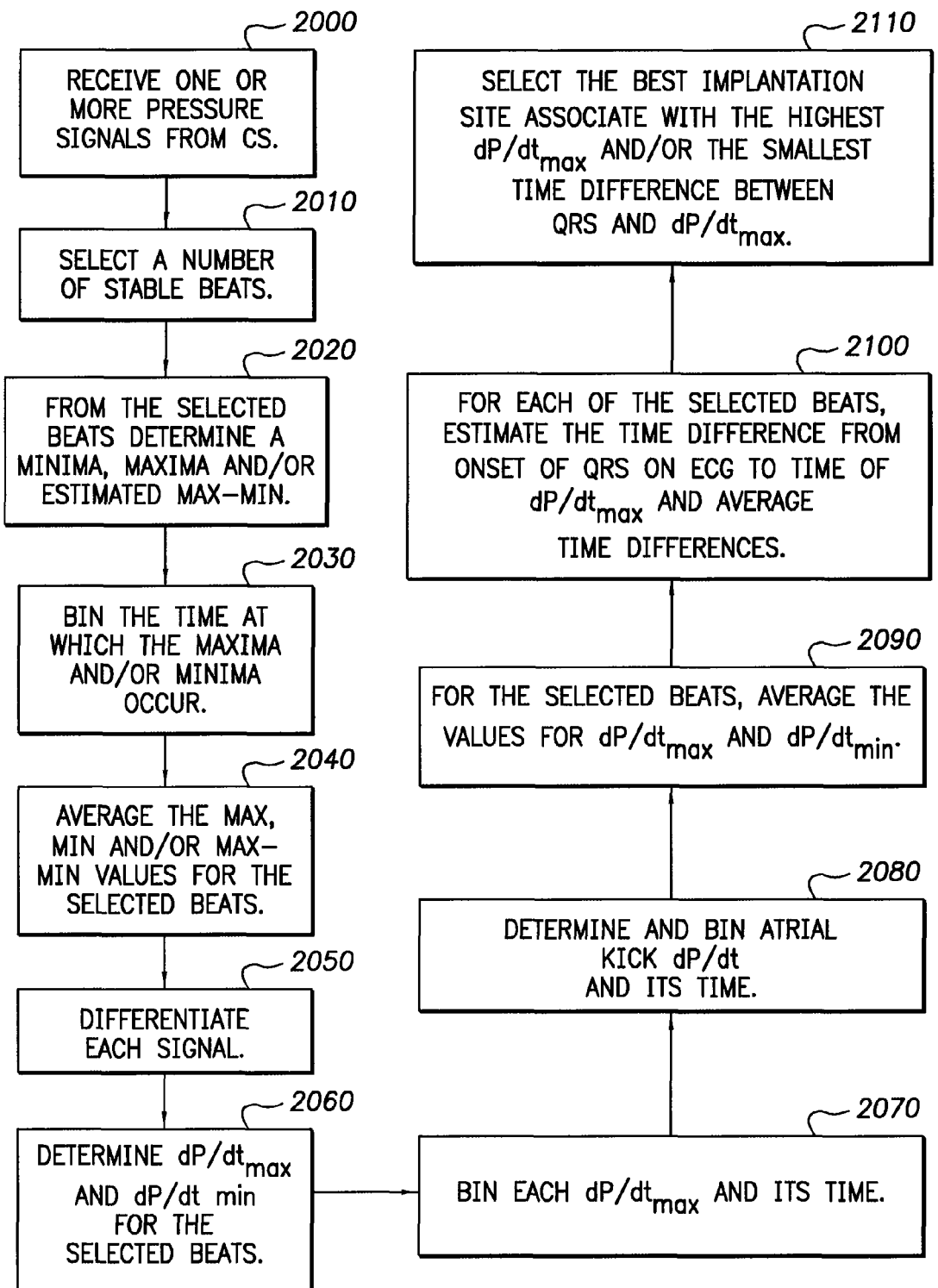
FIG. 21 is a diagram outline a method of employing a delivery tool to optimize CRT using the timing between the maxima and minima dP/dt.

For a discussion regarding a method of analyzing the readings depicted in FIGS. 18-20, reference is made to FIG. 21, which is a flow chart outlining the method. As shown in FIG. 21, a diagnostic machine or device (e.g., a pacer, a pacer programmer, etc.) receives one or more pressure signals from the CS via the pressure sensing capabilities of the above-described lead or introducer tool [block 2000]. In obtaining the pressure signals with the above-described lead or introducer tool, the analysis may be performed occlusively with the CS occluded by an occlusion device on the lead or tool. Alternatively, the analysis may be performed non-occlusively such that the CS is not occluded by the lead or tool or portions thereof.

Where the CS is occluded and the time period of the occlusion is known, a number stable beats is selected [block 2010]. A stable beat may be defined as a beat which, when compared with the next consecutive beat, does not vary more than 10%. The most stable beats may be selected using morphology discrimination or template matching algorithms.

The number of selected beats may be any number depending on the embodiment. For example, in one embodiment, the number of selected beats may be approximately 20. In one embodiment, five beats are counted post occlusion, and then the next 10 to 20 consecutive beats from each signal are binned. In one embodiment, any 10 to 20 consecutive stable beats are selected based on template matching algorithms. In one embodiment, any 10 to 20 beats post occlusion are selected.

From the selected beats, a minima, maxima and/or estimated pressure range is calculated using max-min are determined [block 2020]. The time at which the maxima and/or minima occur is binned [block 2030]. The max, min and/or max-min values for the selected beats are averaged [block 2040].

Each of the signals is differentiated based on a known equation such as the central difference equation [block 2050]. The dP/dt$_{max}$ and dP/dt$_{min}$ for the selected beats is determined [block 2060]. Each dP/dt$_{max}$ and its time is binned [block 2070]. A peak may be observed for each beat and this peak is dP/dt$_{max}$. A low point may also be observed for each beat and this low point is dP/dt$_{min}$.

The atrial kick dP/dt and its time may be determined and binned [block 2080]. Typically, the atrial kick is observed in the original signal, which reflects itself on the differentiated signal as a smaller peak prior to dP/dt$_{max}$. In some embodiments, the atrial kick dP/dt$_{max}$ and its time may be a useful index.

For the selected beats, the values for dP/dt$_{max}$ or dP/dt$_{min}$ are averaged [block 2090]. For each of the selected beats, the time difference from the onset of the QRS on the ECG to the time of dP/dt$_{max}$ is estimated and these time differences are averaged [block 2100].

The implantation site associate with the highest dP/dt$_{max}$ and/or the smallest time difference between QRS and dP/dt$_{max}$ may be selected as the most optimized CRT site [block 2110]. In other words, the highest dP/dt$_{max}$ and shortest time difference between the onset of the QRS and the dP/dt$_{max}$ may be used to indicate that the placement of the electrodes is optimal. Depending on the discretion of the implanter, The best dP/dt| max value and smallest time difference between QRS-dP/dt| max indicate that the electrodes being paced from are optimal. It should be noted that, depending on the discretion of the implanter, the highest dP/dt$_{max}$ and the shortest time between the onset of the QRS and the $dP/dt_{max}$ may be used in conjunction or individually to select the optimal electrode location site.

All the estimated values can be displayed with a snapshot of the pressure signal on the programmer screen or other external device capable to receiving input.

Although the present invention has been described with reference to preferred embodiments, persons skilled in the art will recognize that changes may be made in form and detail without departing from the spirit and scope of the invention.

What is claimed is:

1. A method of measuring pressures in a coronary sinus, the method comprising:
   introducing a distal portion of a lead or tool into the coronary sinus, wherein the distal portion comprises a pressure sensor, and a first occlusion device, and a second occlusion device;
   positioning the pressure sensor near a first junction of the coronary sinus with a first vein intersecting the coronary sinus; and
   expanding the first occlusion device and the second occlusion device so the sensor capability primarily reads the pressure of the first vein intersecting the coronary sinus;
   wherein the pressure sensor is disposed between the first occlusion device and the second occlusion device;
   wherein the first occlusion device is expanded proximal of the first junction and the second occlusion device is expanded distal of the first junction; and
   wherein the expansion of the first and second occlusion devices isolates the sensor from all veins intersecting the coronary sinus, except the first vein; and
   wherein the first vein is any one of a great cardiac vein, a middle cardiac vein, lateral cardiac vein, or a small cardiac vein.

2. The method of claim 1, further comprising detecting ventricular fibrillation by employing the pressure sensor reading.

3. The method of claim 1, further comprising optimizing cardiac resynchronization therapy and/or identifying a non-responder for cardiac resynchronization therapy by employing the pressure sensor reading.

4. The method of claim 1, further comprising optimizing multi-site left ventricle pacing by employing the pressure sensor reading.

5. The method of claim 1, further comprising optimizing right ventricle lead placement by employing the pressure sensor reading.

6. The method of claim 1, further comprising monitoring disease progression by employing the pressure sensor reading.

7. The method of claim 1, wherein the pressure sensor is physically located at the distal portion.

8. The method of claim 1, wherein the pressure sensor is physically located at a proximal portion of the lead or tool and the pressure sensor is in pressure sensing communication with distal portion.

9. The method of claim 1, wherein the at least one occlusion device comprises at least one of a balloon, a one-way valve, a mesh and a membrane.

10. A method of measuring pressures in a coronary sinus, the method comprising:
    introducing a distal portion of a lead or tool into the coronary sinus, wherein the distal portion comprises first and second pressure sensors and at least one occlusion device;
    expanding the at least one occlusion device so the first and second pressure sensors are isolated from each other within the coronary sinus; and
    reading pressure measurements with the first and second pressure sensors which are isolated from each other within the coronary sinus by the at least one occlusion device;
    wherein the first pressure sensor reads a pressure of a first vein intersecting the coronary sinus and the second pressure sensor reads a pressure of a second vein intersecting the coronary sinus; and
    wherein each one of the first vein and the second is any one of a great cardiac vein, a middle cardiac vein, lateral cardiac vein, or a small cardiac vein.

11. The method of claim 10, wherein the at least one occlusion device isolates the first pressure sensor from right atrial pressure and the first pressure sensor reads left ventricular pressure.

12. The method of claim 10, wherein the at least one occlusion device isolates the second pressure sensor from left ventricular pressure and the second pressure sensor reads right atrial pressure.

13. The method of claim 10, wherein the at least one occlusion device isolates the first pressure sensor from the right atrial pressure and the first pressure sensor reads the left ventricular pressure, and the at least one occlusion device isolates the second pressure sensor from the left ventricular pressure and the second pressure sensor reads the right atrial pressure.

14. The method of claim 10, wherein the at least one occlusion device is at least two occlusion devices, the lead or tool further includes a third pressure sensor, and the three pressure sensors take pressure readings that are isolated from each other by the occlusion devices.

15. The method of claim 14, wherein at least one of the pressure sensor readings is the left ventricular pressure.

16. The method of claim 14, wherein at least one of the pressure sensor readings is the right atrial pressure.

17. The method of claim 14, wherein at least two of the pressure sensor readings are the right atrial pressure and the left ventricular pressure.

18. The method of claim 10, wherein the occlusion device is a selectably expandable balloon.

19. The method of claim 10, wherein the pressure sensor is mounted on the distal portion of the lead or tool.

20. The method of claim 10, wherein the pressure sensor is located remotely from the distal portion of the lead or tool.

* * * * *